(12) United States Patent
Alverdy et al.

(10) Patent No.: US 11,571,443 B2
(45) Date of Patent: Feb. 7, 2023

(54) PHOSPHORYLATED TRI-BLOCK COPOLYMERS WITH ANTIMICROBIAL PROPERTIES

(71) Applicants: THE UNIVERSITY OF CHICAGO, Chicago, IL (US); UCHICAGO ARGONNE, LLC, Chicago, IL (US)

(72) Inventors: John C. Alverdy, Glenview, IL (US); Matthew Tirrell, Chicago, IL (US); Olga Y. Zaborina, Brookfield, IL (US); Jun Mao, Chicago, IL (US); Wei Chen, Chicago, IL (US)

(73) Assignee: The University of Chicago, Chicago, IL (US)

( * ) Notice: Subject to any disclaimer, the term of this patent is extended or adjusted under 35 U.S.C. 154(b) by 178 days.

(21) Appl. No.: 16/338,330

(22) PCT Filed: Sep. 29, 2017

(86) PCT No.: PCT/US2017/054424
§ 371 (c)(1),
(2) Date: Mar. 29, 2019

(87) PCT Pub. No.: WO2018/064536
PCT Pub. Date: Apr. 5, 2018

(65) Prior Publication Data
US 2019/0247423 A1    Aug. 15, 2019

Related U.S. Application Data

(60) Provisional application No. 62/483,132, filed on Apr. 7, 2017, provisional application No. 62/402,655, filed on Sep. 30, 2016.

(51) Int. Cl.
| | |
|---|---|
| *A61K 31/77* | (2006.01) |
| *C08G 65/335* | (2006.01) |
| *C08G 81/00* | (2006.01) |
| *A61P 31/04* | (2006.01) |
| *A61P 1/00* | (2006.01) |
| *A61K 47/10* | (2017.01) |
| *A61K 47/34* | (2017.01) |
| *A61K 31/765* | (2006.01) |
| *A61K 9/00* | (2006.01) |
| *A61K 31/80* | (2006.01) |

(52) U.S. Cl.
CPC ............ *A61K 31/77* (2013.01); *A61K 9/0095* (2013.01); *A61K 31/765* (2013.01); *A61K 31/80* (2013.01); *A61K 47/10* (2013.01); *A61K 47/34* (2013.01); *A61P 1/00* (2018.01); *A61P 31/04* (2018.01); *C08G 65/3353* (2013.01); *C08G 81/00* (2013.01)

(58) Field of Classification Search
CPC ...... A61K 31/765; A61K 47/10; A61K 47/34; A61K 31/80; C08G 65/3353; C08G 81/00; A61P 31/04; A61P 1/00
See application file for complete search history.

(56) References Cited

U.S. PATENT DOCUMENTS

| | | | |
|---|---|---|---|
| 9,394,407 B2 | 7/2016 | Ait-Haddou et al. | |
| 9,937,199 B2 | 4/2018 | Alverdy | |
| 2005/0042293 A1 | 2/2005 | Jackson et al. | |
| 2014/0271885 A1 | 9/2014 | Sill et al. | |

FOREIGN PATENT DOCUMENTS

| | | |
|---|---|---|
| WO | WO 2004/047778 A1 | 6/2004 |
| WO | WO 2007/101264 A2 | 9/2007 |
| WO | WO 2010/111294 A1 | 9/2010 |

OTHER PUBLICATIONS

Zaborin et al. (Journal of Antimicrobial Agents and Chemotherapy vol. 58, No. 2, p. 966-977; Feb. 2014) (Year: 2014).*
Marquardt et al. (European Polymer Journal 69 (2015) 319-327) (Year: 2015).*
European Patent Office, Supplementary European Search Report and European Search Opinion, dated Apr. 30, 2020, in European Application No. 17857533.8, 8 pages.
Banerjee et al., "Antifouling Coatings: Recent Developments in the Design of Surfaces that Prevent Fouling by Proteins, Bacteria, and Marine Organisms," Adv. Mater. 23:690-718 (2011).
Bergwitz et al., "Phosphate Sensing," Adv. Chronic. Kidney Dis. 18:132-144 (2011).
Camps et al., "Antifouling Coatings Influence both Abundance and Community Structure of Colonizing Biofilms: a Case Study in the Northwestern Mediterranean Sea," Appl. Environ. Microbiol. 80:4821-4831 (2014).
Dimitriou et al., "A General Approach to Controlling the Surface Composition of Poly(ethylene oxide)-Based Block Copolymers for Antifouling Coatings," Langmuir 27:13762-13772 (2011).
Gao et al., Rationally Designed Dual Functional Block Copolymers for Bottlebrush-like Coatings: In vitro and In vivo Antimicrobial, Antibiofilm, and Antifouling Properties, Acta Biomater. 51:112-124 (2017).

(Continued)

*Primary Examiner* — Anna R Falkowitz

(74) *Attorney, Agent, or Firm* — Leydig, Voit & Mayer, Ltd.

(57) ABSTRACT

The disclosure provides products and methods of treating diseases and disorders involving microbial pathogens, such as intestinal microbial pathogens, e.g., *Pseudomonas aeruginosa*, by administering an effective amount of a phosphorylated polyethylene glycol compound of defined structural organization. Those diseases and disorders characterized by an epithelium attacked by a microbial pathogen are contemplated, including gastrointestinal infections and inflammation, e.g., treatment of intestinal or esophageal anastomosis or treatment or suppression of anastomotic leakage.

24 Claims, 17 Drawing Sheets

Specification includes a Sequence Listing.

(56) References Cited

OTHER PUBLICATIONS

International Search Report and Written Opinion from International Application No. PCT/US2017/054424 dated Dec. 22, 2017.

Jensen et al. "Rhlr Expression in Pseudomonas Aeruginosa is Modulated by the Pseudomonas Quinolone Signal via PhoB-Dependent and -Independent Pathways," J. Bacteriol. 188:8601-8606 (2006).

Kolate et al., "PEG—a Versatile Conjugating Ligand for Drugs and Drug Delivery Systems," J. Control. Release 192:67-81 (2014).

Li et al., "Synthesis of Amphiphilic Copolymer Brushes: Poly(Ethylene Oxide)-graft-Polystyrene," J. Polym. Sci. A Polym. Chem. 44:4361-4371 (2006).

Liechty et al., "Polymers for Drug Delivery Systems," Annu. Rev. Chem. Biomol. Eng. 1:149-173 (2010).

Luong et al., "Emergence of the P2 Phenotype in Pseudomonas aeruginosa PAO1 Strains Involves Various Mutations in mexT or mexF," J. Bacteriol. 196:504-513 (2014).

Mangold et al., "Hetero-Multifunctional Poly(ethylene glycol) Copolymers with Multiple Hydroxyl Groups and a Single Terminal Functionality," Macromol. Rapid Comm. 31:258-264 (2010).

Mao et al., "De Novo Synthesis of Phosphorylated Triblock Copolymers with Pathogen Virulence-Suppressing Properties That Prevent Infection-Related Mortality," ACS Biomater. Sci. Eng. 3(9):2076-2085 (2017).

Merz et al., "Pilus Retraction Powers Bacterial Twitching Motility," Nature 407:98-102 (2000).

Price et al., "Selective Decontamination of the Digestive Tract and Oropharynx: After 30 Years Of Debate is the Definitive Answer in Sight?," Curr. Opin. Grit. Care. 22:161-166 (2016).

Teillant et al., "Potential Burden of Antibiotic Resistance on Surgery and Cancer Chemotherapy Antibiotic Prophylaxis in the USA: a Literature Review and Modelling Study," Lancet Infect. Dis. 15:1429-1437 (2015).

Vale et al., "Beyond Killing: Can We Find New Ways to Manage Infection?," Evol. Med. Public Health 1:148-157 (2016).

Vilar et al., "Polymers and Drug Delivery Systems," Curr. Drug Deliv. 9:367-394 (2012).

Wang et al., "Investigation of the Role of Hydrophilic Chain Length in Amphiphilic Perfluoropolyether/Poly(ethylene glycol) Networks: Towards High-performance Antifouling Coatings," Biofouling 27:1139-1150 (2011).

Wu et al., "High-molecular-weight Polyethylene Glycol Prevents Lethal Sepsis due to Intestinal Pseudomonas Aeruginosa," Gastroenterology 126:488-498 (2004).

Xiao et al., "MvfR, a Key Pseudomonas Aeruginosa Pathogenicity LTTR-class Regulatory Protein, Has Dual Ligands," Mol. Microbiol. 62:1689-1699 (2006).

Zaborin et al., "Membership and Behavior of Ultra-Low-Diversity Pathogen Communities Present in the Gut of Humans during Prolonged Critical Illness," mBio 5(5):e01361-01314 (2014).

Zaborin et al., "Phosphate-Containing Polyethylene Glycol Polymers Prevent Lethal Sepsis by Multidrug-Resistant Pathogens," Antimicrobial Agents and Chemotherapy 58(2)7966-977 (2014).

Zaborin et al., "Pseudomonas Aeruginosa Overrides the Virulence Inducing Effect of Opioids When it Senses an Abundance of Phosphate," Plos One 7:e34883 (2012).

Zaborin et al., "Red Death in Caenorhabditis Elegans Caused by Pseudomonas Aeruginosa PAO1," Proc. Natl. Acad. Sci. USA 106:6327-6332 (2009).

Zaborina et al., "Dynorphin Activates Quorum Sensing Quinolone Signaling in Pseudomonas Aeruginosa," Plos Pathog. 3(3):e35 (2007).

Zaborina et al., "Host Stress and Virulence Expression in Intestinal Pathogens: Development of Therapeutic Strategies Using Mice and C. elegans," Curr. Pharm. Design 17:1254-1260 (2011).

Zhou et al., "Amphiphilic Triblock Copolymers with PEGylated Hydrocarbon Structures as Environmentally Friendly Marine Antifouling and Fouling-release Coatings," Biofouling 30:589-604 (2014).

Zhou et al., "Synthesis, Characterization, and In Vivo Evaluation of Poly(Ethylene Oxide-co-Glycidol)-Platinate Conjugate," Eur. J. Pharm. Sci. 41:464-472 (2010).

\* cited by examiner

A.

B.

SEQUENCE LISTING

```
<160> NUMBER OF SEQ ID NOS: 2

<210> SEQ ID NO 1
<211> LENGTH: 24
<212> TYPE: DNA
<213> ORGANISM: Pseudomonas aeruginosa
<220> FEATURE:
<221> NAME/KEY: misc_feature
<223> OTHER INFORMATION: PCR forward primer PstS F

<400> SEQUENCE: 1
cacctatccc aaaacccctg gtca                                          24

<210> SEQ ID NO 2
<211> LENGTH: 24
<212> TYPE: DNA
<213> ORGANISM: Pseudomonas aeruginosa
<220> FEATURE:
<221> NAME/KEY: misc_feature
<223> OTHER INFORMATION: PCR reverse primer PstS R

<400> SEQUENCE: 2
caaacgcttg agtttcatgc cttg                                          24
```

PHOSPHORYLATED TRI-BLOCK COPOLYMERS WITH ANTIMICROBIAL PROPERTIES

CROSS-REFERENCE TO RELATED APPLICATIONS

This application is a U.S. national phase of International Application No. PCT/US17/54424, filed Sep. 29, 2017, which claims the priority benefit under 35 U.S.C. § 119(e) of Provisional U.S. Patent Application No. 62/402,655, filed Sep. 30, 2016 and Provisional U.S. Patent Application No. 62/483,132, filed Apr. 7, 2017, the disclosures of which are incorporated herein by reference in their entireties.

GOVERNMENT SUPPORT

This invention was made with government support under R01GM062344 awarded by the National Institutes of Health and under DE-AC02-06CH11357 awarded by the Department of Energy. The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 51283A_Seqlisting.txt; 781 bytes, created Sep. 25, 2017.

FIELD

The disclosure relates generally to the fields of medical treatment, prevention or suppression of epithelial diseases and disorders including infections and inflammation.

BACKGROUND

The promiscuous use of antibiotics had led to the emergence of antibiotic resistance at an unprecedented pace and continues to place patients at risk for life-threatening infections following major surgery. Many if not most of the pathogens that cause these infections use the intestinal tract as their primary site of colonization. Although surgeons routinely decontaminate the intestinal tract with antibiotics prior to surgery to prevent infection, this practice carries the unintended consequence of causing antibiotic resistance. Furthermore, overuse of antibiotics destroys the microbiome that normally protects against high risk pathogens. A more evolutionarily stable strategy to this problem would be to develop compounds that suppress pathogen virulence without affecting the growth of the pathogenic organisms, thereby preserving the microbiome. In this manner, bacterial pathogenicity could be contained and the colonization resistance of the normally protective microbiota preserved.

Phosphate is a key universal cue for bacteria to either enhance their virulence, for example when local phosphate is scarce, or to suppress virulence when phosphate is abundant. Phosphate can become depleted in the mammalian gut following physiologic stress and serves as a major trigger for colonizing bacteria to express virulence and invasiveness. This process cannot be reversed with oral or intravenous inorganic phosphate, as phosphate is nearly completely absorbed in the proximal small intestine.

One obstacle to using commercially available PEG 15-20 (Sigma) is that PEG 15-20 is not a pure tri-block polymer but rather a mixture of polymers of varying molecular weights. This situation limits the ability to further interrogate the molecular mechanisms by which the polymers protect both in vitro and in vivo, and the limited content of phosphate inhibits the opportunity to further improve the efficacy of the polymers.

In view of the foregoing observations, it is apparent that needs continue to exist in the art for products and methods useful in treating, preventing or suppressing diseases and disorders characterized by a pathogenic microbial attack on an epithelium.

SUMMARY

The disclosure provides materials and methods for treating, preventing or suppressing diseases and conditions associated with pathogenic microbe-mediated epithelial diseases or disorders such as gastrointestinal infections or inflammation, or gastrointestinal anastomoses or anastomotic leaks, such as esophageal or intestinal anastomoses or anastomotic leaks. The materials for use in such circumstances are phosphorylated polyethylene glycol compounds of a defined structure, such as an A-B-A triblock copolymer structure (ABA-PEG-Pi). Notably, the ABA-PEG-Pi materials of the disclosure comprise a hydrophobic core such as a diphenylmethyl moiety and the materials exhibit a substantially similar molecular weight wherein about 80%, 90%, 95%, 96%, 97% 98%, 99%, 99.5% or 99.9% of the ABA-PEG-Pi molecules have the same molecular weight (plus or minus 5% or 10%). The particular structure of the ABA-PEG-Pi and the relatively constant structure result in effects on epithelial cell diseases and disorders mediated by obligate or opportunistic microbial pathogens.

One aspect of the disclosure is drawn to a triblock copolymer comprising: (a) a hydrophobic core; and (b) at least two polyethylene glycol chains wherein at least one polyethylene glycol chain is a phosphorylated polyethylene glycol comprising more than two phosphate groups. The hydrophobic core is a "B" block copolymer and the PEG chains are generally considered "A" block copolymers using the triblock copolymer terminology of the disclosure. It is recognized that triblock copolymers can be indicated as having an A-B-A or an A-B-A' triblock copolymer structure depending on whether the at least two PEG chains are the same or not. In some embodiments, at least two polyethylene glycol chains are phosphorylated polyethylene glycol chains comprising more than two phosphate groups. In some embodiments, the hydrophobic core is a carbocyclic or heterocyclic ring, including embodiments wherein the ring is aromatic, such as a single ring or a plurality of rings. In some embodiments, the hydrophobic core is a diphenylmethyl moiety. In some embodiments, the hydrophobic core is a 4,4'-(propane-2,2-diyl)diphenolate salt. In some embodiments, the copolymer has a molecular weight of at least 8,000 daltons, at least 12,000 daltons, at least 15,000 daltons, at least 16,000 daltons, at least 20,000 daltons, or is between 15,000-20,000 daltons. In some embodiments, the copolymer is in solution. In some embodiments, the dispersity (Ð) of the triblock copolymer disclosed herein is less than or equal to 1.10. In some embodiments, the triblock copolymer is a phosphorylated form of ABA-PEG-PGly or ABA-PEG-PEEGE.

Another aspect of the disclosure is directed to a method of producing the triblock copolymer comprising (a) covalently attaching at least two polyethylene glycol chains to a hydrophobic core comprising a carbocyclic or heterocyclic ring; and (b) covalently attaching at least two phosphate groups to at least one polyethylene glycol chain. In some embodiments, at least two polyethylene glycol chains are each covalently attached to at least two phosphate groups.

Yet another aspect of the disclosure is a method of treating anastomosis comprising administering a therapeutically effective amount of a composition comprising a triblock copolymer disclosed herein to a subject in need. In some embodiments, the triblock copolymer has a molecular weight of at least 8,000 daltons, 12,000 daltons, 15,000 daltons, 16,000 daltons, 20,000 daltons, or between 15,000-20,000 daltons.

Still another aspect of the disclosure is a method of treating anastomotic leakage comprising administering a therapeutically effective amount of a composition comprising a triblock copolymer disclosed herein to a subject in need. In some embodiments, the triblock copolymer has a molecular weight of at least 8,000 daltons, 12,000 daltons, 15,000 daltons, 16,000 daltons, 20,000 daltons, or between 15,000-20,000 daltons.

In another aspect, the disclosure provides a method of preventing anastomotic leakage comprising administering an effective amount of a composition comprising a triblock copolymer disclosed herein to a subject at risk of anastomotic leakage. In some embodiments, the triblock copolymer has a molecular weight of at least 8,000 daltons, 12,000 daltons, 15,000 daltons, 16,000 daltons, 20,000 daltons, or between 15,000-20,000 daltons.

Yet another aspect of the disclosure is directed to a method of suppressing anastomotic leakage comprising administering an effective amount of a composition comprising a triblock copolymer disclosed herein to a subject at risk of anastomotic leakage. In some embodiments, the triblock copolymer has a molecular weight of at least 8,000 daltons, 12,000 daltons, 15,000 daltons, 16,000 daltons, 20,000 daltons, or between 15,000-20,000 daltons.

Another aspect of the disclosure is drawn to a method of inhibiting, e.g., preventing, microbial virulence, such as the virulence of *Pseudomonas aeruginosa* or the virulence of *Enterococcus faecalis*. Virulence is herein defined as the relative ability of a microorganism, such as *P. aeruginosa* or *E. faecalis*, to cause disease, which is a measure of the degree of pathogenicity. Stated alternatively, virulence reflects the capability of a microorganism to cause disease. Virulence in *P. aeruginosa* can be characterized by the P2 (or virulent) phenotype, wherein *P. aeruginosa* one or more of the following features: produces toxin(s), exhibits swarming motility, activates expression of the quorum-sensing system (QS), has elevated expression of PstS, and/or increases production of pyocyanin and/or pyoverdin. Virulence in *E. faecalis* can be characterized by increased collagenase production. Accordingly, the disclosure provides a method of inhibiting microbial virulence in the gastrointestinal tract comprising administering an effective amount of a composition comprising a triblock copolymer as disclosed herein to a subject at risk of inducing microbial virulence. In some embodiments, the triblock copolymer has a molecular weight of at least 8,000 daltons, 12,000 daltons, 15,000 daltons, 16,000 daltons, 20,000 daltons, or between 15,000-20,000 daltons. In some embodiments, the microbe is *Pseudomonas aeruginosa*. In some embodiments, the microbe is *Enterococcus faecalis*.

The methods of inhibiting microbial virulence are related to another aspect of the disclosure providing a method of treating a gastrointestinal microbe capable of developing a virulent phenotype comprising administering an effective amount of a composition comprising a triblock copolymer as disclosed herein to a subject comprising the gastrointestinal microbe. In some embodiments, the triblock copolymer has a molecular weight of at least 8,000 daltons, 12,000 daltons, 15,000 daltons, 16,000 daltons, 20,000 daltons, or between 15,000-20,000 daltons. In some embodiments, the gastrointestinal microbe capable of developing a virulent phenotype is *Pseudomonas aeruginosa*. In some embodiments, the gastrointestinal microbe capable of developing a virulent phenotype is *Enterococcus faecalis*.

Other features and advantages of the disclosure will become apparent from the following detailed description, including the drawing. It should be understood, however, that the detailed description and the specific examples, while indicating embodiments, are provided for illustration only, because various changes and modifications within the spirit and scope of the disclosure will become apparent to those skilled in the art from the detailed description.

BRIEF DESCRIPTION OF THE DRAWING

FIG. 10(B) shows cell proliferation relative to cecal crypt depth for mice drinking water lacking any phosphorylated PEG (PC 1-3), mice drinking water containing 3% PPi6 (PPi6 1-3), or mice drinking water containing 1% ABA-PEG20k (ABA-PEG20k-Pi20 1-3), wherein "1-3" refers to individual mice subjected to the indicated conditions. The height of proliferating cells relative to cecal crypt depth were 50.54±1.711 m for water only, 35.12±1.332 m for 3% PPi6, and 39.01±0.909 m for 1% ABA-PEG20k.

DETAILED DESCRIPTION

Figure 1:
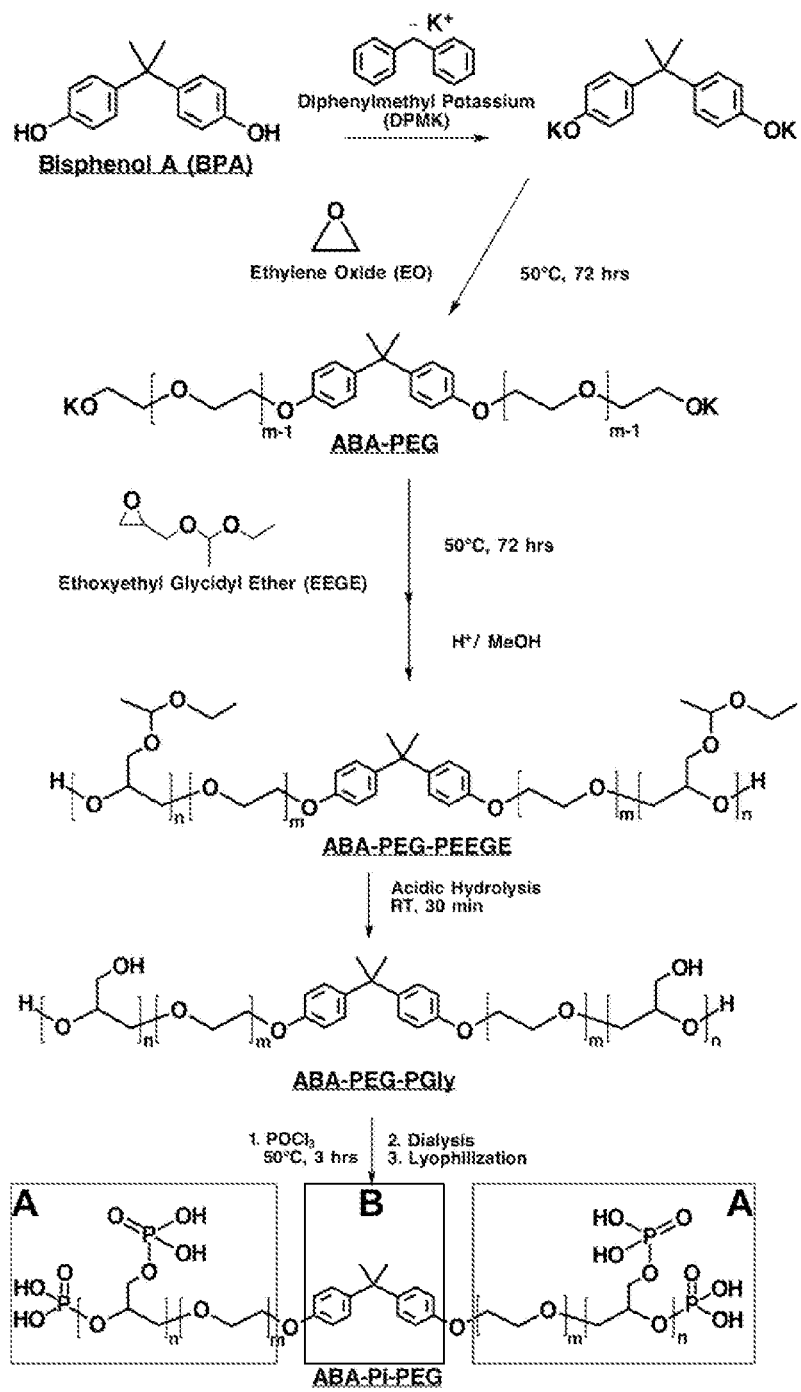
FIG. 1. Reaction scheme for the synthesis of ABA-Pi-PEG block copolymers.

A phosphorylated polyethylene glycol compound of high molecular weight allows phosphate to be distributed along the entire gut and into the distal intestine where microbes such as bacteria are most abundant. The phosphorylated polyethylene glycol compounds of the disclosure have a triblock copolymer structure of ABA, with "A" referring to any polyethylene glycol, or derivative thereof, that is at least 8,000 daltons, 12,000 daltons, 15,000 daltons, 16,000 daltons, 20,000 daltons, or is between 15,000-20,000 daltons. The "B" component of the triblock structure is a hydrophobic compound capable of covalent linkage to two PEG molecules of the disclosure, or derivatives thereof. Exemplary hydrophobic cores are bisphenol A (BPA) and bisphenol E (BPE).

In discussing the compounds of the disclosure, and compositions comprising such compounds, the following terminology is used. "ABA" refers to the triblock structural organization of the compounds, with two like polymers, e.g., PEG, bracketing a "B" structure that is a hydrophobic core such as any aliphatic, carbocyclic, heterocyclic, or aromatic structure that is hydrophobic, e.g. any of the bisphenols. "PEG" refers to polyethylene glycol, and "PEG-Pi" refers to a phosphorylated polyethylene glycol. "EEGE" is ethoxyethyl glycidyl ether and "PEEGE" is polyethoxyethyl glycidyl ether. As described below, EEGE is de-protected and, once de-protected, EEGE groups become hydroxy groups and the structure is referred to as a polyglycidol, such as ABA-PEG-PGly. Compounds identified as ABA-PEG10k-E8, ABA-PEG16k-E12, and ABA-PEG20k-E18 refer to triblock copolymers having the ABA structure with 8 EEGE groups (E8) and PEG groups of 10k in ABA-PEG8k-E8. For ABA-PEG16k-E12, the compound has the ABA structure with 12 EEGE groups (E12) and PEG groups of 16k. In like manner, ABA-PEG20k-E18 has an ABA structure with 18 EEGE groups and PEG groups of 20k. For compounds identified as ABA-PEG10k-GO1, ABA-PEG16k-G14 and ABA-PEG20k-G20, "G10" refers to 10 hydroxyl groups created by de-protection of EEGE (the "G" is a reference to the compound as a polyglycidol), while "G14" and "G20" refer to 14 and 20 hydroxyl groups, respectively. Compounds defined as ABA-PEG10k-Pi10, ABA-PEG16k-Pi14, and ABA-PEG20k-Pi20 refer to compounds having the ABA triblock copolymer structure with 10, 14, or 20 phosphoryl groups (e.g., phosphate groups), respectively, resulting from phosphorylation of a polyglycidol. Consistent with the naming convention explained above, PEG10k, PEG16k, and PEG20k refer to PEG groups of 10k, 16k and 20k, respectively. It is apparent that the number of functional groups (e.g., EEGE) ultimately rendered amenable to phosphorylation can vary in the compounds according to the disclosure, and the size of PEG molecules bearing those functional groups can vary, including PEG molecules in a compound totaling at least 8,000 daltons, at least 12,000 daltons, at least 15,000 daltons, at least 16,000 daltons, at least 20,000 daltons or between 15,000-20,000 daltons.

The phosphate content of compounds delivered to the intestine is particularly important for any protective effect because local phosphate concentrations support bacterial growth while at the same time suppressing bacterial virulence [28]. The mechanism underlying this effect involves phosphosensory/phosphoregulatory circuits that are a universal feature of most bacteria and play a key role in virulence [29].

Figure 7:
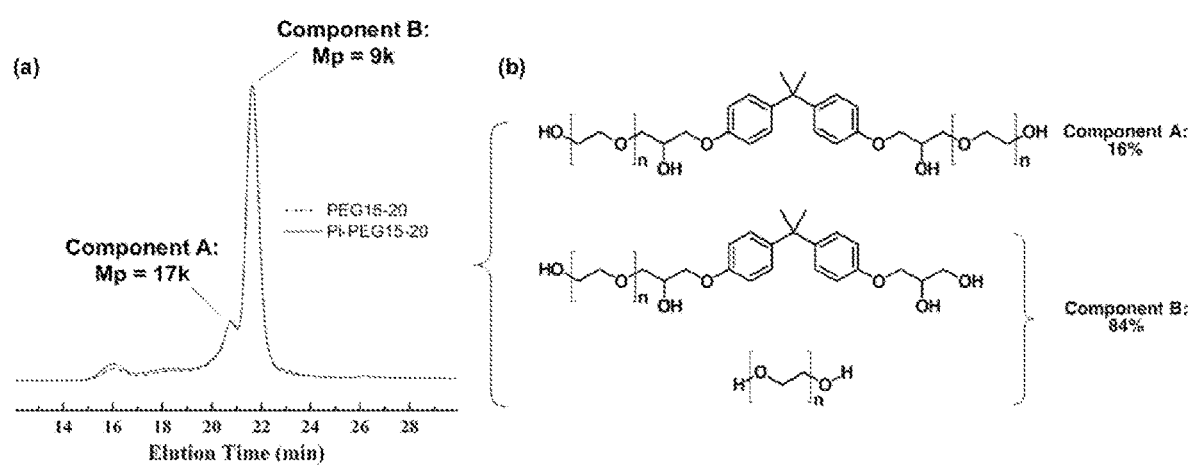
FIG. 7. Composition analysis of PEG15-20 (Sigma) and Pi-PEG15-20. (A) GPC traces of commercial PEG15-20 and its phosphorylated product Pi-PEG15-20 in 0.1 M $NaNO_3$ (25° C., 1.0 ml/minute) indicate that PEG15-20 is a mixture of homopolymers and copolymers with ABA and AB structures. (B) Analysis reveals that 16% of PEG15-20 contained ABA structure, as calculated from the integration area of the GPC curve.

Analysis of PEG15-20 (Sigma) showed that it was not a pure tri-block polymer but rather a mixture of polymers of varying molecular weights including ABA triblock, AB diblock and homopolymer poly(ethylene glycol) structures (FIG. 7). In contrast to these impure mixtures of polymers of differing molecular weights, disclosed herein is the de novo synthesis of polymers with a well-defined ABA structure, the phosphorylation of which yielded compounds with a defined number of phosphorus atoms (phosphate groups). Results demonstrated highly effective anti-virulence properties of the synthesized phosphorylated polymers with defined ABA structure and phosphate content against the model opportunistic pathogen *Pseudomonas aeruginosa*.

The disclosure will be more fully understood by reference to the following examples, which detail exemplary embodiments of the disclosure. The examples should not, however, be construed as limiting the scope of the disclosure.

EXAMPLES

Example 1

Materials and Methods.

Materials. Bisphenol A (BPA, >99%, Aldrich), naphthalene (99%, Aldrich), diphenylmethane (99%, Aldrich), and phosphorus oxychloride ($POCl_3$, 99%, Aldrich) were used as received. Ethylene oxide (EO, >99%, lecture bottle, Praxair) and Ethoxyethyl glycidyl ether (EEGE, 97%, Synthonix) were treated with di-n-butylmagnesium for 20 minutes, and distilled into Schlenk flasks before use. Tetrahydrofuran (THF, HPLC, inhibitor free, Aldrich) was purified with solvent purification system (Mbraun SPS-800) and distilled from a sodium naphthalenide solution directly before use. Diphenylmethylpotassium (DPMK) was prepared as described. Initially, a potassium naphthalenide solution was prepared in dry THF with 1:4 molar ratio of naphthalene to potassium. After stirring for 12 hours, 0.66 mole equivalents of diphenylmethane were introduced into the solution via syringe, and the solution was allowed to stir at room temperature for at least 12 hours prior to use.

Synthesis of phosphorylated PEG-based block copolymers with a hydrophobic core. Sequential Anionic Polymerization of ABA-PEG-PEEGE. A series of ABA-PEG-PEEGE were synthesized by the sequential anionic polymerization of EO and EEGE in a custom heavy-wall glass reaction flask on a Schlenk line. In a typical reaction, BPA (251 mg, 1.1 mmol) dissolved in 120 mL anhydrous THF at 0° C. under dry nitrogen atmosphere, was titrated with DPMK to form the initiator, followed by addition of the first monomer EO (22.0 g, 500 mmol). After stirring for 1 hour, the mixture was heated to 50° C. and reacted for 3 days to attain complete conversion of the EO monomer. Then, the second monomer EEGE (2.9 g, 19.8 mmol) was injected into the flask and allowed to react for another 3 days. The polymerization was terminated with methanol and the polymer was recovered by precipitation in cold diethyl ether. Different chain lengths of EO and EEGE are adjusted by the feed ratio of [EO]/[Initiator] and [EEGE]/[Initiator].

Hydrolysis of ABA-PEG-PEEGE. Hydrolysis of EEGE segments of block copolymer was carried out in THF with 4 wt % of HCl and stirred at room temperature for 30 minutes. The polymers were then purified by precipitating in cold hexane and finally dried under vacuum at 60° C. to get a yellowy wax-like product, i.e., ABA-PEG-PGly (PGly: Poly glycerol). The disappearance of peaks at 4.70 ppm (q, 1H), 1.29 ppm (d, 3H), 1.19 ppm (t, 3H) in $^1$H-NMR confirmed the success of de-protection.

Phosphorylation of ABA-PEG-PGly. ABA-PEG-Pis (Pi: Poly phosphoric acid) were prepared by phosphorylation of ABA-PEG-PGly, which was performed in a flame-dried flask under dry nitrogen atmosphere. ABA-PEG-PGly was dissolved in anhydrous THF at 50° C., and a ten-fold equivalent molar amount of $POCl_3$ was added at once via gas-tight syringe. The solution was stirred under nitrogen pressure for 3 hours, and then quenched by the addition of a small amount of water. After evaporation of THF and dialysis against Milli-Q water, the sample was lyophilized to give a white flocculent product. $^{31}$P-NMR ($D_2O$): δ −0.18 ppm.

Synthesis of phosphorylated PEG-based block copolymers without a hydrophobic core (PEG-Pi). The synthetic strategy of PEG-Pi is quite similar to that of ABA-PEG-Pi, with the exception that the polymerization started with hydrophilic ethylene glycol instead of hydrophobic BPA, as shown in Scheme 2. First, PEG-PEEGE was prepared by starting with ethylene glycol. Next, polymerizing through the sequential adding of EO and EEGE and then using the same hydrolysis process (as used to obtain PEG-PGly) and the same phosphorylation process, PEG-Pi was obtained.

Characterization of block copolymers. $^1$H and $^{31}$P-NMR spectra were obtained at a Bruker Ultrashield Plus 500 MHz spectrometer and referenced internally to solvent proton signal. Apparent molecular weights and dispersity (Ð) were characterized with a gel permeation chromatography (GPC) system equipped with a Waters 1515 pump, a Wyatt Optilab T-rEX differential refractive index (RI) detector, and a Waters 2998 photodiode array (PDA) detector. For ABA-PEG-PEEGEs, ABA-PEG-PGlys, PEG-PEEGEs and PEG-PGlys, THF was used for elution at 35° C. with an elution rate of 0.8 mL/minute. Three Waters Styragel columns were used and calibrated by polystyrene standards (Aldrich). ABA-PEG-Pis and PEG-Pis were measured in 0.1 M $NaNO_3$ (aq) at 25° C. with an elution rate of 1.0 mL/minute on the same setup, except three Waters Ultrahydrogel columns in series were used and calibrated by PEO standards (Aldrich). Regarding dispersity of a polymer, monodispersed means the polymer itself, meaning all the polymer chains have nearly identical chain lengths. For amphiphilic block copolymers in selective solvent, for example ABA-PEG-Pi in aqueous solutions, water is a good solvent for a hydrophilic block, but a poor solvent for a hydrophobic block. In this situation, a block copolymer can self-assemble into aggregated structures, such as micelles, vesicles, and the like. Sometimes, micelles/vesicles and much larger structures further aggregated from micelles/vesicles can co-exist in the same solution.

Even for block copolymers with very narrow dispersity, under some circumstances, the block copolymers can form non-uniform structures in solutions. Even when a block copolymer forms uniform aggregated structures in solution, these structures can be monodispersed, meaning all the aggregates have nearly identical size and shape.

Biological tests. Bacterial strains. *Pseudomonas aeruginosa* strains MPAO1-P1 and MPAO1-P2 [16] were used in all experiments. The MPAO1-P1 strain and its derivative mutant ΔPvdD were used to create the reporter constructs, MPAO1-P1/pstS-EGFP and ΔPvdD/pstS-EGFP.

Construction of pSensor-PstS-EGFP. The promoter region of the pstS gene (*P. aeruginosa* MPAO1) was cloned in a pSensor vector. As noted in Example 4, PstS is the phosphate-binding component of the ABC-type transporter complex pstSACB involved in phosphate transport into the bacterial cytoplasm. The pSensor consists of a pUCP24 vector backbone and Gateway C. 1 cassette (Invitrogen) in frame with the EGFP reporter gene (derived from pBI-EGFP) cloned into the Sma1 and Pst1/Hind III sites of the pUCP24 MCS region, respectively. The region upstream of pstS was amplified by PCR (Platinum PCR SuperMix (Invitrogen) using primers PstS_F: CACCTATCC-CAAAACCCCTGGTCA (SEQ ID NO:1) and PstS_R: CAAACGCTTGAGTTTCATGCCTTG (SEQ ID NO:2), and cloned into the Gateway entry vector (pCR8/GW/Topo kit (Invitrogen)). Nucleotide sequence and orientation of the inserts were confirmed by sequencing, inserts were transferred into pSensor vector via LR reaction using Gateway LR Clonase II Enzyme Mix (Invitrogen). Throughout the study, vector constructs were propagated in One Shot TOP10 Chemically Competent *E. coli* cells. Gentamycin (100 µg/ml) selection was used for pUCP24 and pSensor and Ampicillin (100 µg/ml) for pBI-EGFP vectors. The QIA-GEN Plasmid Mini Kit (Qiagen) was used for plasmid DNA extraction.

PstS expression. *P. aeruginosa* MPAO1-P1/pstS-EGFP or ΔPvdD/pstS-EGFP were grown on tryptic soy agar plates supplemented with 100 µg/ml gentamicin (Gm100) overnight. A few colonies from the overnight plates were used to inoculate liquid TSB+Gm100 for overnight growth. The overnight culture was used to inoculate fresh TSB+Gm100 at 1:100 dilution and grown to $OD_{600\ nm}$=0.5. Cells were pelleted by centrifugation at 3300×g for 5 minutes, and washed twice with defined citrate media (DCM: sodium citrate, 4.0 g/L (Sigma, S4641), $(NH_4)_2SO_4$, 1.0 g/L (Sigma, A4915), $MgSO_4 \cdot 7H_2O$, 0.2 g/L (Fisher, M63-50). DCM medium is limited in both phosphate and iron. Potassium phosphate buffer, pH 6.0 (PPB), was used for phosphate supplementation. The supplementation of DCM with PPB 0.1 mM was defined for phosphate limitation (DCM-Pi0.1), and with PPB 25 mM for phosphate abundance (DCM-Pi25). Washed cells were resuspended in DCM-Pi0.1+Gm100 or DCM-Pi25+Gm100, respectively, and grown overnight. In experiments carried out to test the phosphorylated polymers, bacterial cells were washed in DCM-Pi0.1 and resuspended in DCM-Pi0.1+Gm100 supplemented with 2 mM ABA-PEG-Pis or ABA-PEG-PGlys and adjusted to pH 6.0 with KOH. After overnight growth, fluorescence (excitation 485/10, emission 528/20) and absorbance (600 nm) were measured with a FLx800 fluorescent reader (Biotek Instruments). Fluorescence readings were normalized to absorbance. Culture conditions were 37° C. with shaking at 180 rpm (C25 Incubator Shaker, New Brunswick Scientific, Edison, N.J.).

Pyocyanin production during low-phosphate conditions. *P. aeruginosa* MPAO1-P2, which is known to produce higher amounts of pyocyanin than MPAO1-P1 [16], was used in this set of experiments. The design of the experiments was similar to the experiments described above for PstS expression except they were performed in the absence of Gm in the DCM media. 2 µM $Fe^{3+}$ (1 µM $Fe_2(SO_4)_3$) was added to the media in order to enhance the production of pyocyanin. Pyocyanin was extracted by chloroform followed by re-extraction in the 0.2N HCl and measured at $OD_{520}$ nm as previously described [17]. Before extraction, cell density was measured by the absorbance at 600 nm, and pyocyanin values were normalized to bacterial cell density.

Pyocyanin production following exposure to virulence activating factor u-50,488, kappa opioid agonist. *P. aeruginosa* was known to be triggered to express enhanced virulence when exposed to kappa opioid, host factors known to be released into the gut during physiologic stress [17]. *P. aeruginosa* MPAO1-P1, which is highly sensitive to U-50,488, was used in these experiments.

MPAO1-P1 was grown on tryptic soy agar plates overnight, and a few colonies were used to inoculate liquid TSB for overnight growth. Overnight cultures were used to inoculate fresh TSB at 1:100 dilution and allowed to grow out for 1 hour. Next, 200 µM U-50,488 (Sigma) was added, and growth was continued for 10 hours. Pyocyanin was extracted and measured as described above.

Pyoverdin production. *P. aeruginosa* MPAO1-P1 was used in these experiments. The design of the experiments was similar to the experiments described above for PstS expression except they were performed without Gm in the DCM media. Pyoverdin was measured by fluorescence (400/10 excitation, 460/40 emission) using FLx800 fluorescent reader (Biotek Instruments). Data were normalized to cell density measured as absorbance at 600 nm.

*Caenorhabditis elegans* killing assays. *C. elegans* N2 nematodes provided by the *Caenorhabditis* Genetic Center (CGC), University of Minnesota, were used in these experiments. Synchronization and pre-fasting of worms was performed by transferring them onto plain plates with kanamycin as previously described [3]. *P. aeruginosa* MPAO1-P1 was grown overnight in tryptone/yeast extract medium (TY, tryptone, 10 g/L; yeast extract, 5 g/L) and diluted at 1:100 in 0.1×TY (TY diluted 10-fold with water). Potassium phosphate buffer, pH 6.0, was included in the 0.1×TY to a final concentration of 0.1 mM. After 1 hour of growth, the kappa-opioid receptor agonist U-50,488 was added to a final concentration of 50 µM followed by 2 hours growth as previously described [18, 19]. Two ml of the microbial culture was adjusted to room temperature and poured in the 30-mm-diameter dishes into which pre-fasting nematodes (10 nematodes per plate) were transferred. *P. aeruginosa* was grown overnight in TY media diluted 1:100 in either 0.1×TY or 0.1×TY containing polymers at 2 mM (or 5% in selected experiments, as indicated) final concentration and adjusted to pH 5.2 with KOH. Plates were incubated at room temperature, without shaking, and mortality was defined if worms did not respond to the touch of a platinum picker.

Statistical analyses. All data are from 3 or more replicates and presented as the mean with standard deviation presented as error bars. Statistical analysis was performed using SigmaPlot software. In *C. elegans* experiments, Long-rank (Mantiel-Cox) test (GraphPad Prizm 7) was used with significance accepted as a p-value <0.05. In in vitro experiments, Student t-tests were used and significance determined to be p-value <0.05.

Scanning electron microscopy (SEM). *P. aeruginosa* MPAO1 was grown in tryptic soy broth (TSB) overnight. Overnight cultures (2 ml) were centrifuged at 6,000 rpm, 5 minutes, room temperature, and pellets were gently washed (3 times) with DCM-Pi0.1 (see description of PstS expression, above). Washed pellets were suspended in 1 ml of DCM-Pi0.1 or 2 mM ABA-PEG20k-Pi20 or 2 mM PEG20k-Pi20. ABA-PEG20k-Pi20 and PEG20k-Pi20 solutions were prepared in DCM-Pi0.1. The pH of these phosphorylated polymers is around 2-3, therefore, the pH was adjusted by KOH to DCM-Pi0.1 (pH5.5). Bacteria were grown for 4 hours, then cells were pelleted by centrifugation at 6,000 rpm, 5 minutes, room temperature, and gently washed (3 times) with phosphate-buffered saline (PBS). Bacterial cells were then dropped onto glass coverslips coated with poly-L-lysine. Cells were fixed in 3% glutaraldehyde buffered with 0.1 M phosphate buffer, pH 7.2, washed with 0.1 M phosphate buffer, and dehydrated in a graded ethanol solution in water (30% increased gradually to 100%; 20 minutes each). The samples were dried with a Leica CPD300 critical point dryer and coated with Pt(80)/Pd(20) to a thickness of 2 nm using a Cressington sputter coater, model 208HR. SEM images were obtained using a Zeiss Merlin FE-SEM with an accelerating voltage of 1 kV and a working distance of 3 mm.

Example 2

Design and Synthesis of Phosphorylated PEG-Based Block Copolymer with a Hydrophobic Core (ABA-PEG-Pi).

The purpose of this study was to develop phosphate-containing PEG-based block copolymers with a defined ABA structure and molecular weight and to identify their effectiveness in suppressing microbial virulence using biological tests. The ABA structure and phosphate were shown to be involved in providing the biologic function of Pi-PEG 15-20. However, molecular weight measurements (FIG. 7) indicated that both Pi-PEG 15-20 and its precursor PEG 15-20 were polydisperse, i.e., PEG 15-20 contained component A, 16% of block copolymer with ABA structure, and component B, 84% of block copolymer with an AB structure and a PEG homopolymer. The phosphorylated homopolymer failed to show a protective effect in biological tests, and separating it from the original polydisperse mixture to refine the active component proved implausible, since it has an almost identical molecular weight to the block copolymer with an AB structure and since they both are water-soluble. As such, this complex composition presented challenges to determine the mechanism of protection of each component. Therefore, a rational design of an alternative PEG with uniform composition and similar structure to the active components in Pi-PEG 15-20 was required in order to achieve both the key features of the ABA structure and controllable phosphate content.

PEG chains contain only one or two terminal hydroxyl groups suitable for further functionalization. To incorporate more hydroxyl groups per polymer chain, sequential anionic copolymerization of ethylene oxide (EO) with a functional epoxide monomer, ethoxy ethyl glycidyl ether (EEGE), an ethoxyl ethylacetal protected glycidol was used to acquire block copolymers with polyethylene oxide as backbone, along with controllable hydroxyl groups [20-22]. As depicted in FIG. 1, the design of ABA-PEG-Pi involved the initial synthesis of symmetric block copolymer ABA-PEG-PEEGE from Bisphenol A, followed by de-protection of PEEGE block to recover the pendant hydroxyl groups, and the subsequent functionalization of all the hydroxyl groups of the block copolymer with phosphate This strategy allowed access to a series of block copolymers with defined ABA architecture, which consisted of three distinctive segments: (i) B group represents the small, yet very hydrophobic bis-phenol A moiety at the polymer center, (ii) PEG blocks adjacent to the bi-aromatic center formed the inert spacer and the inner part of hydrophilic A groups. As an integral part of the architecture, the chain length of the PEG block played a key role in the hydrophobicity/hydrophilicity balance of the whole polymer, (iii) phosphorylated polyglycidol block acts as the outer part of hydrophilic A groups, offering biological functionality and defined phosphate content.

Figure 2:
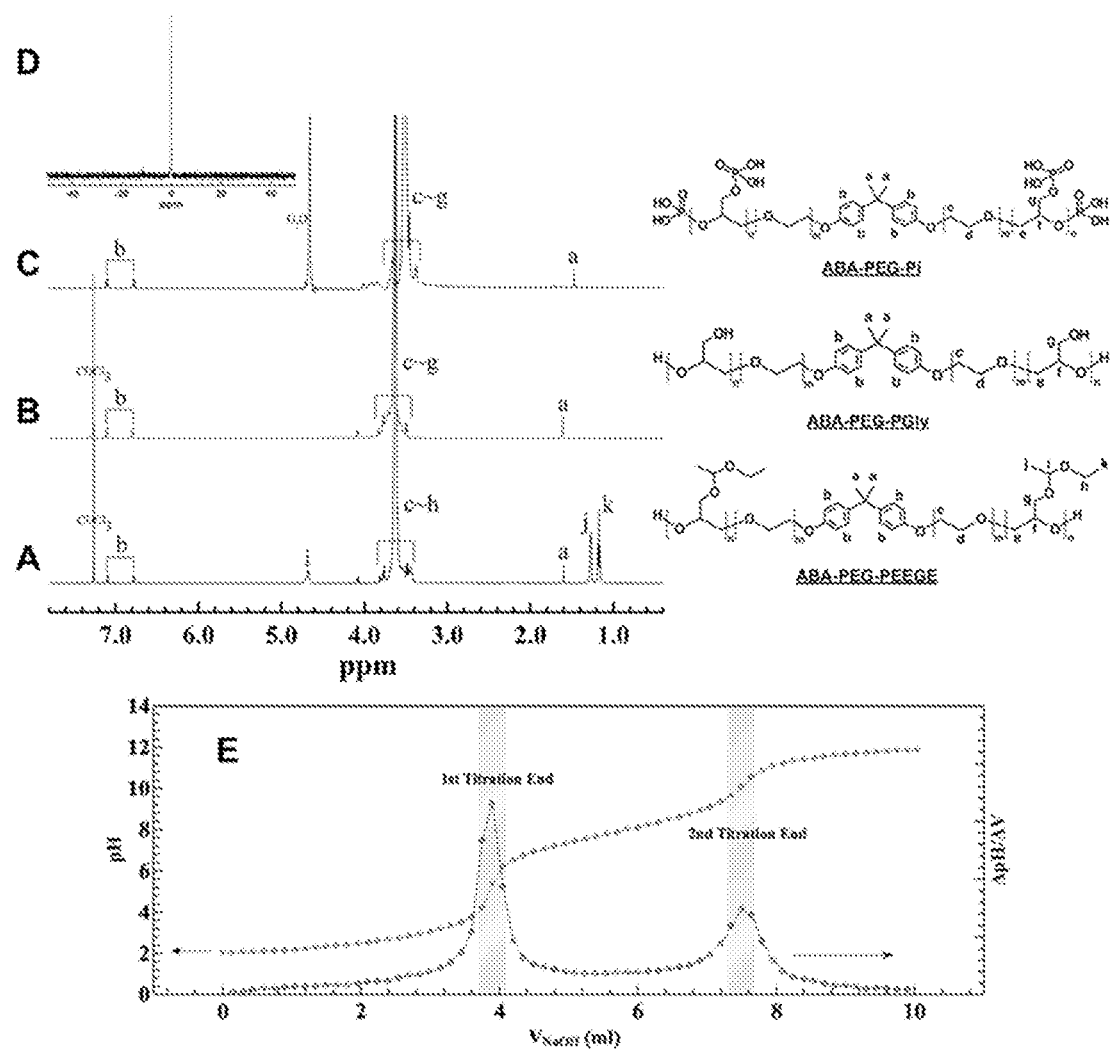
FIG. 2. $^1$H-NMR spectra of (A) ABA-PEG20k-E18, (B) ABA-PEG20k-G20, (C) ABA-PEG20k-Pi20, (D) $^{31}$P-NMR spectrum of ABA-PEG20k-Pi20, and (E) Titration curve of ABA-PEG20k-Pi20 with NaOH solution. 20k is the designed molecular weight of PEG block; E18 means the designed repeating units of EEGE block is 18; G20 means the designed repeating units of Glycerol is 20. Pi20 means the designed repeating units of the phosphorylated Glycerol block is 20.

Three ABA-PEG-Pis, ABA-PEG10k-Pi10, ABA-PEG16k-Pi14 and ABA-PEG20k-Pi20 were synthesized. 10k, 16k and 20k corresponded to the different molecular weight of PEG block. By incorporating more repeating units of phosphate (10, 14 to 20 repeating units in the above phosphorylated HMW PEGs, respectively), almost identical molar concentration of phosphate can be maintained for each block copolymer (e.g., for 1 g of each block copolymer, the molar concentration of phosphate were 0.78, 0.77 and 0.80 mmol, respectively, for ABA-PEG10k-Pi10, ABA-PEG16k-Pi14 and ABA-PEG20k-Pi20). Initiated from bis-phenoxide, the sequential anionic ring-opening polymerization of EO and EEGE was successful. This can be confirmed by the chemical shifts seen in $^1$H-NMR spectra (FIG. 2A): a ($\delta$=1.60, 6H) and b ($\delta$=6.78, 7.09, 8H) were assigned to the dimethyl and aromatic groups of BPA, c~h ($\delta$=3.43-3.80) were assigned to protons of the main chain and lateral chains, and i ($\delta$=4.70, 1H), j ($\delta$=1.29, 3H) and k ($\delta$=1.19, 3H) were ascribed to the methyl protons of the EEGE moiety. Furthermore, the chain length of the PEG and PEEGE blocks could be varied by adjusting the feed ratio of EO and EEGE monomer to the initiator BPA, and the composition of the block copolymer can be determined by the integrals of specific signals from each block in 1H-NMR spectra. The degree of polymerization of PEEGE block ($N_{EEGE}$) can be calculated by the integration ratio:

$$N_{EEGE} = 8 * \frac{I_i}{I_b},$$

where $I_i$ and $I_b$ are the integration of Peak i and b in FIG. 2, respectively.

The degree of polymerization of PEG block ($N_{EG}$) was given by $$N_{EG} = 2 * \frac{I_{c-h} - 7 N_{EEGE} * I_i}{I_b}$$

where $I_{c-h}$ is the integration of Peak c~h in FIG. 2. Detailed molecular weights characterization results for all the samples are summarized in Table 1.

TABLE 1

List of polymers synthesized in this study.

|  |  | $M_a^a$ (kDa) GPC | $M_a$ (kDa) NMR | $Đ^b$ | $N_{EEGE}^c$ | $N_{hydroxyl}^d$ | $N_{phosphate}^e$ |
|---|---|---|---|---|---|---|---|
| ABA-PEG-PEEGE | ABA-PEG10k-E8 | 26.1 | 12.4 | 1.05 | 8.0 | | |
|  | ABA-PEG16k-E12 | 31.7 | 17.8 | 1.07 | 11.6 | | |
|  | ABA-PEG20k-E18 | 35.9 | 24.6 | 1.04 | 17.5 | | |
| ABA-PEG-PGly | ABA-PEG10k-G10 | 23.2 | 11.9 | 1.06 | | 10.0 | |
|  | ABA-PEG16k-G14 | 27.8 | 17.1 | 1.06 | | 13.6 | |
|  | ABA-PEG20k-G20 | 31.1 | 23.3 | 1.05 | | 19.5 | |
| ABA-PEG-Pi | ABA-PEG10k-Pi10 | 12.9 | 12.3 | 1.10 | | | 9.8 ± 0.2 |
|  | ABA-PEG16k-Pi14 | 13.7 | 18.2 | 1.08 | | | 13.8 ± 0.8 |
|  | ABA-PEG20k-Pi20 | 25.8 | 25.9 | 1.07 | | | 19.5 ± 0.5 |

Nomenclature of the polymers: Take ABA-PEG10k-E8/ABA-PEG10k-G10/ABA-PEG10k-Pi10 as examples. 10k is the designed molecular weight of PEG block; E8 means the designed repeating units of EEGE block is 8; G10 means the designed repeating units of Glycerol is 10. Because hydrolysis of EEGE block released 8 alcohol groups plus 2 primary alcohol groups at the chain ends, the total is 10 repeating units for Glycerol; Pi10 indicates that the designed repeating units of the phosphorylated Glycerol block is 10. Other polymer designations disclosed herein follow this nomenclature scheme.

a: ABA-PEG-PEEGE and ABA-PEG-PGly samples were measured in THF against PS standards; ABA-PEG-Pi samples were measured in 0.1 M $NaNO_3$ against PEO standards.
b: Measured by GPC.
c: Calculated from NMR.
d: $N_{hydroxyl}=N_{EEGE}+2$ primary alcohol groups at chain ends, NMR confirmed the complete de-protection of EEGE repeat units.
e: $N_{phosphate}$ of ABA-PEG-Pi samples were determined by phosphoric acid titration determinations.

EEGE was chosen to be the outer block, due to the advantages that: (i) it has a similar main chain to PEG and can be co-polymerized with EO through an anionic mechanism, (ii) this structural similarity also indicates that PEG-PEEGE should be non-toxic and safe, which is relevant to the use of ABA-PEG-PEEGE in biomedical applications, and (iii) the protective ethoxy ethylacetal groups can be easily removed by acidic hydrolysis, yielding pendant hydroxyl group in each repeating unit, offering perfect functionalization sites for phosphorylation. Complete hydrolysis could be verified by the disappearance of specific EEGE signals i, j and k, comparing FIG. 2A and FIG. 2B. Finally, phosphorylation was performed by the reaction between ABA-PEG-PGly samples with phosphorus oxychloride, which was shown to be highly effective. The existence of phosphate in ABA-PEG-Pi samples can be verified by the chemical shift δ=–0.18 ppm in the $^{31}$P-NMR spectrum (FIG. 2D). The number-average molecular weights of ABA-PEG-Pi measured by GPC for ABA-PEG10k-Pi10, ABA-PEG16k-Pi14 and ABA-PEG20k-Pi20 were 12.9k, 18.7k and 25.8k, respectively, and corresponded well with those determined from NMR results also shown in Table 1 (12.8k, 18.2k and 25.0k, respectively), which further confirmed that the degree of functionalization of the available hydroxyl groups was complete.

In order to further identify the degree of phosphorylation, phosphoric acid titration experiments were performed to identify the average number of phosphate groups per polymer chain. Briefly, 0.1M of sodium hydroxide (NaOH) solution was titrated into the ABA-PEG-Pi/PEG-Pi solution, and the pH changes were monitored using a pH meter with automatic temperature compensation. FIG. 2E shows a typical titration curve. The pH value of the solution increased with the gradual addition of NaOH (left axis), two buffer region (gray column area) were observed; after simply taking the first derivation (right axis), two equivalence points were clearly visualized. The data show the characteristic behavior of a diprotic acid, and the relatively broader peaks in the buffer region was consistent with the behavior of a poly(phosphoric acid). These results are in accordance with the structure of phosphoric acid units on the polymer chain. The average number of phosphate groups per polymer chain $N_{phosphate}$ can be calculated by equation:

$$N_{phosphate} = \frac{[NaOH] * V_1}{m/M_n} \text{ or } N_{phosphate} = \frac{[NaOH] * V_2}{2m/M_n}$$

where [NaOH] is the concentration of sodium hydroxide solution, $V_1$ and $V_2$ are the volume of sodium hydroxide solution consumed at first' titration end and second titration end, respectively. m is the mass of ABA-PEG-Pi polymer used in the titration, and $M_n$ is the number average molecular weight of ABA-PEG-Pi polymer. Theoretically, the volume of NaOH solution consumed at the second titration end ($V_2$) should be twice that found at the first titration end ($V_1$). In the experiment disclosed herein, $V_2$ is a little bit lower than $2V_1$. Without wishing to be bound by theory, this may be due to the dissociation constant difference between the phosphoric acid units at the chain ends and those far from the chain ends.

Through the above method, the average number of phosphate groups per polymer chain $N_{phosphate}$ for ABA-PEG10K-Pi10, ABA-PEG16K-Pi14 and ABA-PEG20k-Pi20 were determined to be 9.8±0.2, 13.0±0.8, and 19.5±0.5, respectively. These results confirm that phosphorylation of available hydroxyl groups was complete.

Example 3

Synthesis of Phosphorylated PEG-Based Block Copolymer without Hydrophobic Core (PEG-Pi).

Figure 8:
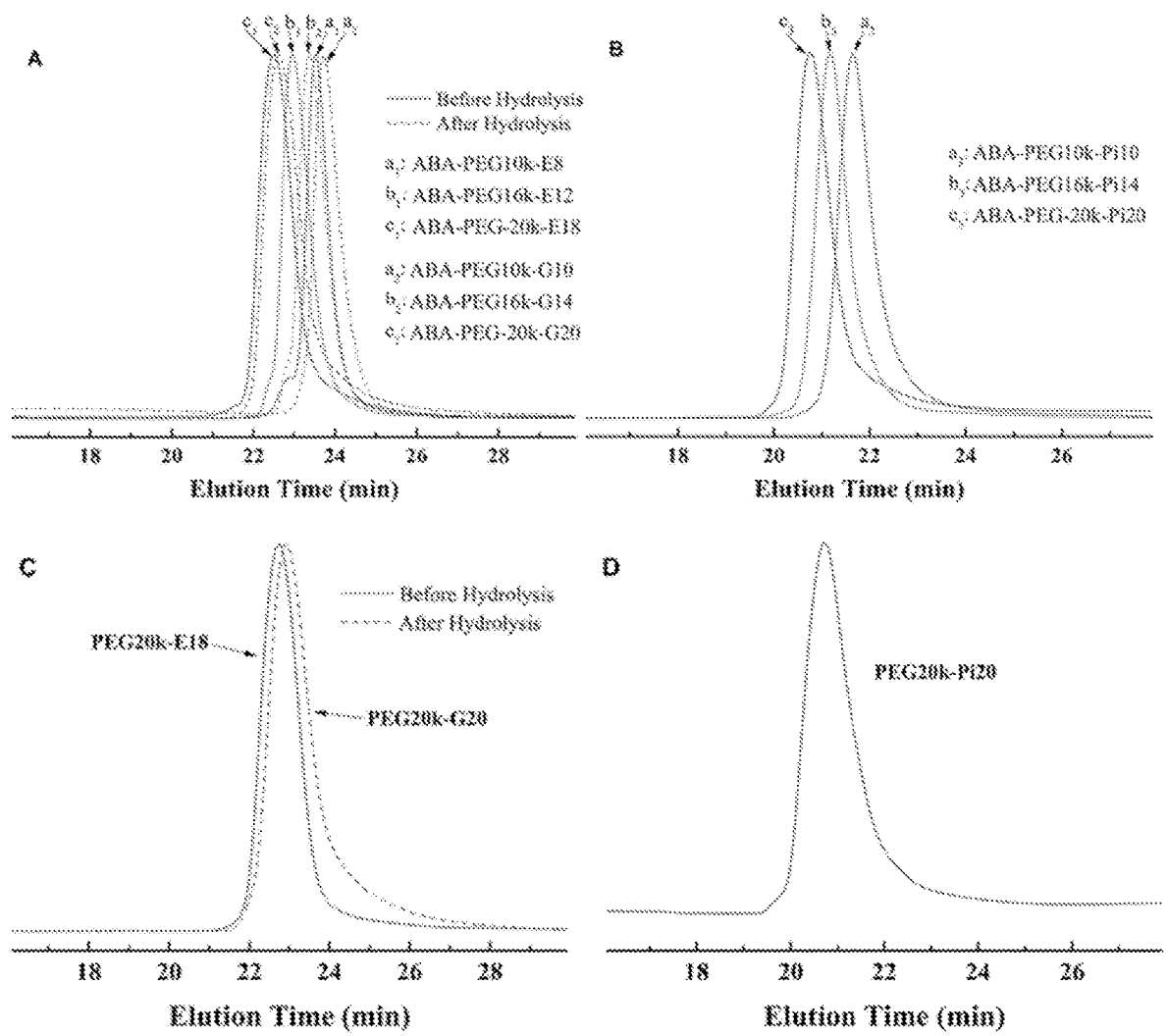
FIG. 8. GPC traces of (A) ABA-PEG-PEEGE, ABA-PEG-PGly in tetrahydrofuran (THF; 35° C., 0.8 ml/minute); (B) ABA-PEG-Pi in 0.1 M NaNO$_3$ (25° C., 1.0 ml/minute); (C) PEG-PEEGE, PEG-PGly in THF (35° C., 0.8 ml/minute); and (D) PEG-Pi in 0.1 M NaNO$_3$ (25° C., 1.0 ml/minute).
Figure 13:
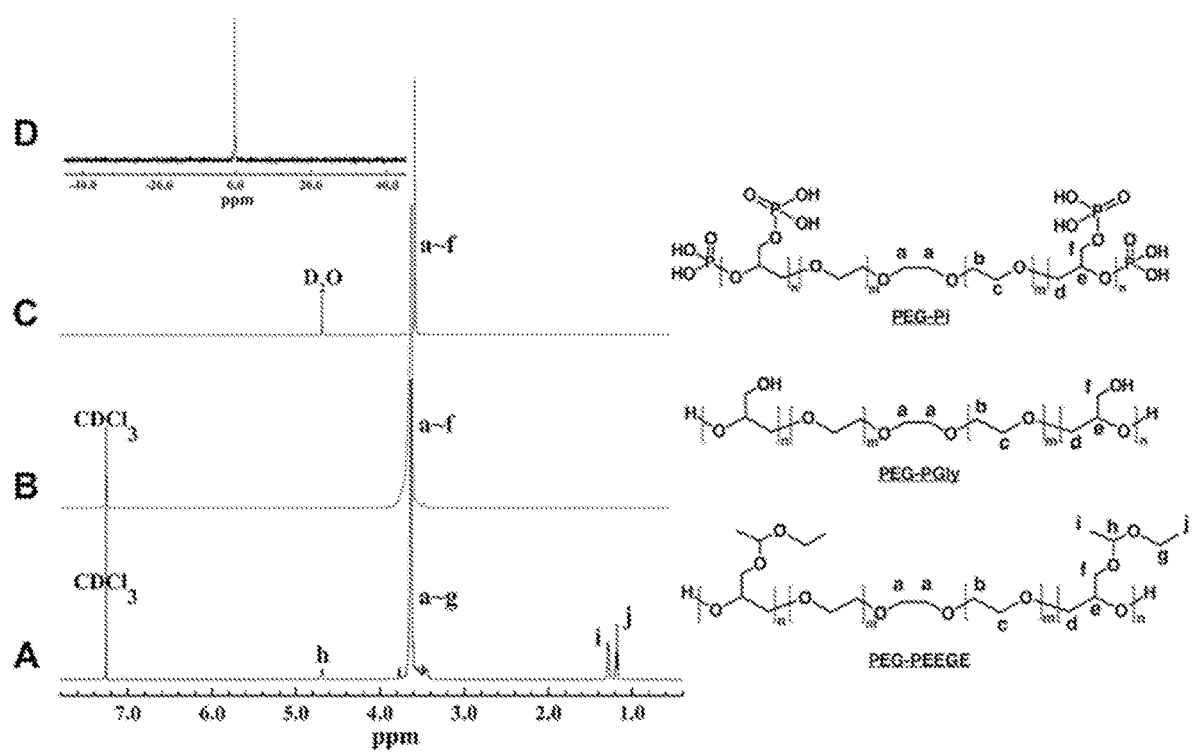
FIG. 13. $^1$H-NMR spectra of (A) PEG20k-E18; (B) PEG20k-G20; (C) PEG20k-Pi20; and (D) $^{31}$P-NMR spectrum of PEG20k-Pi20.
Figure 15:
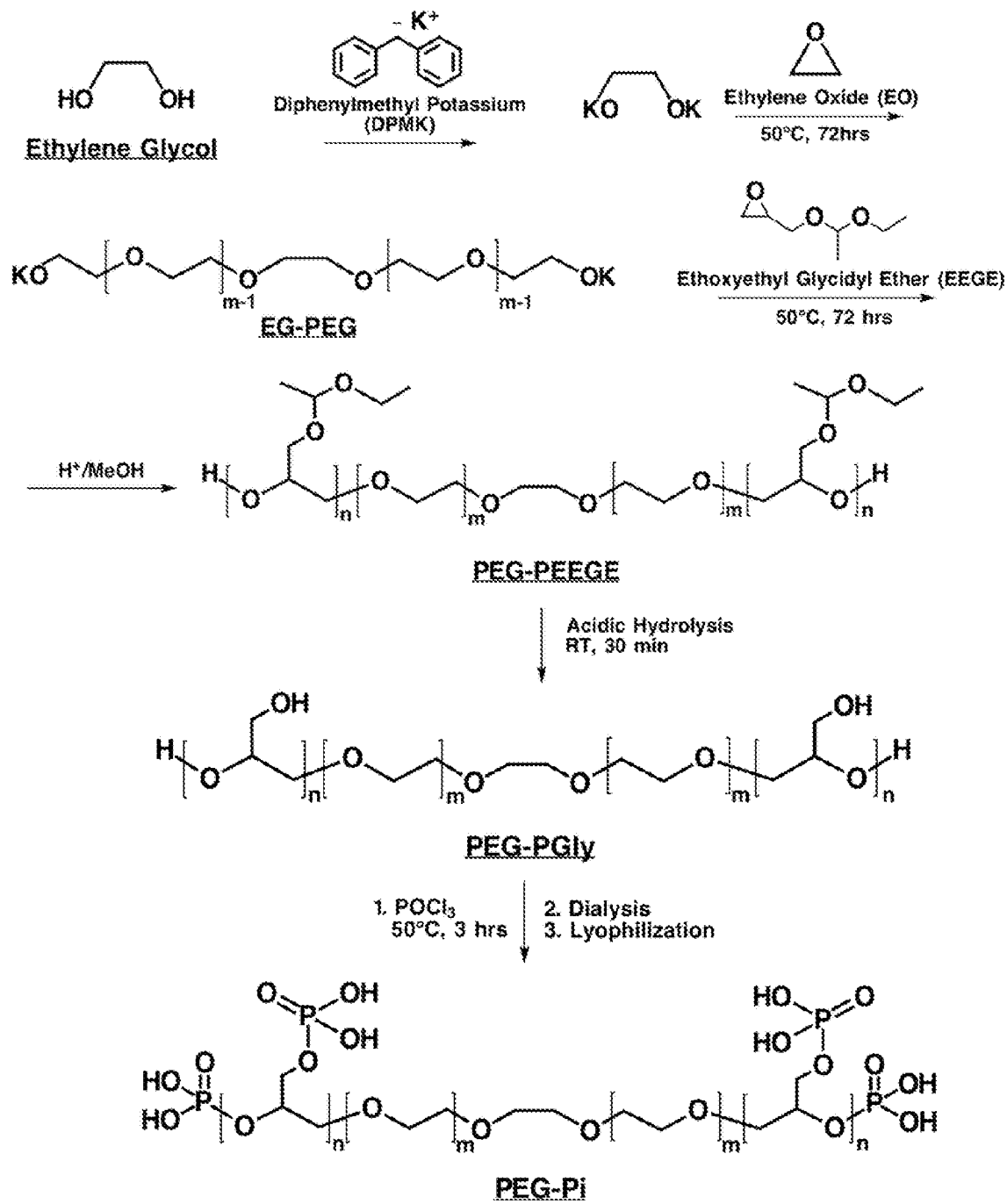
FIG. 15. Strategy for the synthesis of PEG-Pi polymers.

In order to demonstrate the structural importance of the hydrophobic moiety, another phosphate-containing PEG-based block copolymer without a hydrophobic core, namely PEG-Pi, was synthesized for comparison. The only structural difference between PEG-Pi and ABA-PEG-Pi is the center moiety (FIG. 10): for PEG-Pi, the center moiety is ethylene glycol; whereas for ABA-PEG-Pi, it is BPA. As depicted in FIG. 15, the synthesis of PEG-Pi started from ethylene glycol, through the same sequential anionic ring-opening polymerization of EO and EEGE, hydrolysis and phosphorylation, producing the final product PEG-Pi. As with ABA-PEG20k-Pi20, 20k corresponded to the designed molecular weight of the PEG block, 20 was the designed number of repeating units of phosphate incorporated into each chain. GPC elution curve analyses demonstrated the uniform composition in the synthesized polymers (FIG. 8). The polymerization, hydrolysis and phosphorylation were similarly monitored by NMR spectroscopy. The spectra are shown in FIG. 13. a~g ($\delta$=3.43-3.80) are ascribed to protons of the main chain and lateral chains, h ($\delta$=4.70, 1H), i ($\delta$=1.29, 3H) and i ($\delta$=1.19, 3H) are assigned to the methyl protons of the EEGE moiety. The disappearance of signals h. i and j confirmed complete hydrolysis of the compound, and the chemical shift $\delta$=−0.17 ppm in the $^{31}$P-NMR spectrum verified the existence of phosphate in PEG20k-Pi20. The average number of phosphate groups per polymer chain $N_{phosphate}$ for PEG20k-Pi20 calculated from phosphoric acid titration determinations was 19.8±0.3, indicating nearly 100% phosphorylation. The number-average molecular weights measured by GPC for PEG20k-E18, PEG20k-G20 and PEG20k-Pi20 were 36.5k, 31.6k and 26.2k, respectively, which are very close to the values of ABA-PEG20k-Pi20, making PEG20k-Pi20 an excellent analogue to ABA-PEG20k-Pi20. Detailed molecular weight characterization results, GPC elution curves and NMR spectra are summarized in Table 2 and in FIGS. 8 and 13.

It is also important to note that, due to the use of a living anionic polymerization technique, the dispersity (Ð) of all these PEG-based block copolymers were kept narrow (<1.10). Significant broadening of the corresponding GPC traces was not observed even after de-protection and phosphorylation (FIG. 8), indicating excellent control over molecular weight, architecture and the number of phosphate units that were desired for biological tests.

Example 4

ABA-PEG-Pis Inhibit Phosphate Signaling in *P. aeruginosa* Under Phosphate-Limiting Conditions.

Figure 3:
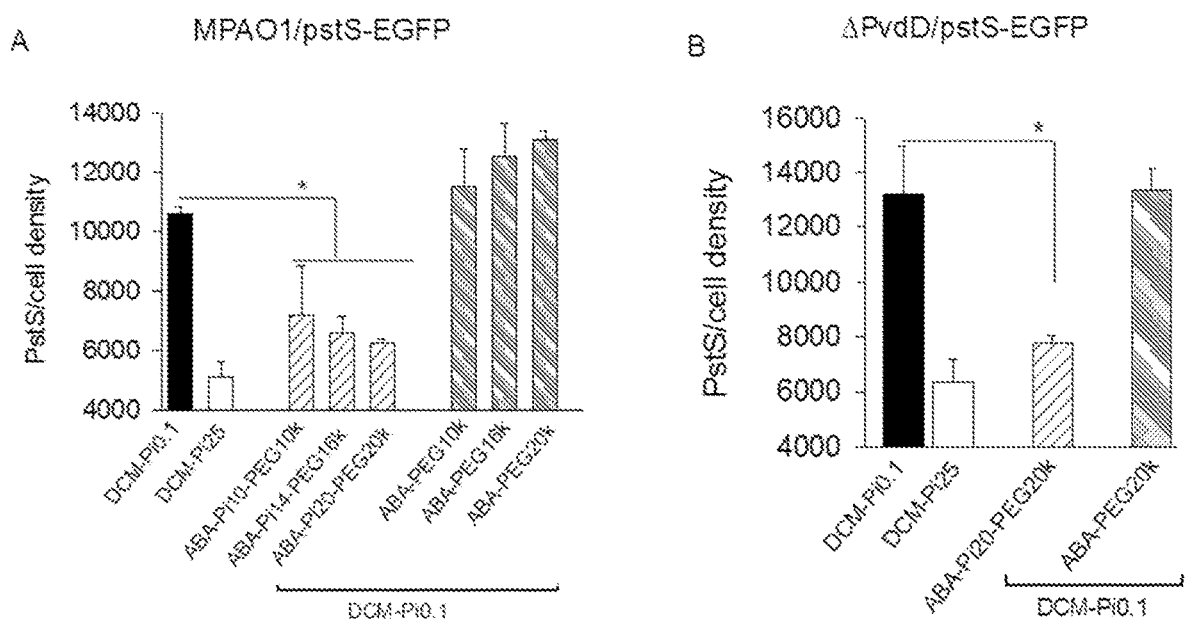
FIG. 3. ABA-Pi-PEGs significantly decrease PstS expression in *P. aeruginosa*. PstS expression in MPAO1/pstS-EGFP (A), and ΔPvdD/pstS-EGFP (B). n=3 per group, *p<0.01. Columns represent average values, and error bars—standard deviations.
Figure 9:
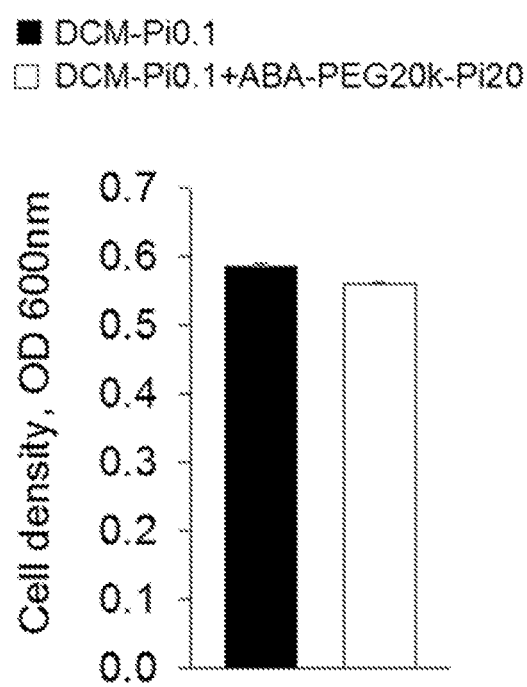
FIG. 9. ABA-Pi20-PEG2k does not inhibit growth of *P. aeruginosa*. Absorbance at $OD_{600\,nm}$ measured in overnight culture of *P. aeruginosa* MPAO1/psts-EGFP in DCM-Pi0.1 and DCM-Pi0.1 supplemented with 2 mM ABA-PEG20k-Pi20. Results present mean data of three biological replicates.

Multiple biological tests were performed to assess the functionality of the synthesized polymers as anti-virulence compounds. Expression of the phosphate transport protein PstS in *P. aeruginosa* was used as a biomarker to determine phosphate availability of the various polymers. If PstS expression was increased, it served as a proxy indicating that extracellular phosphate was depleted and unavailable within the phosphorylated compound. On the other hand, if PstS was observed to be decreased, it indicated that *P. aeruginosa* detected sufficient phosphate availability in the test compound. PstS is the phosphate-binding component of the ABC-type transporter complex pstSACB involved in phosphate transport into the bacterial cytoplasm. PstS is known to be induced by phosphate limitation and suppressed in a phosphate-rich extracellular environment. In order to track the expression of PstS, the pSensor-PstS-EGFP plasmid (see Example 1) was electroporated in the *P. aeruginosa* MPAO1-P1 strain to yield the MPAO1-P1/pstS-EGFP reporter strain. The expression of PstS was detected by fluorescence (excitation 485/10, emission 528/20) normalized to cell density measured by the absorbance at 600 nm. As a control, PstS expression in *P. aeruginosa* grown in low phosphate- and high phosphate-defined citrated media (DCM) was used. Data indicated, as expected, that PstS expression was increased in low-phosphate medium and was nearly completely suppressed in medium containing 25 mM inorganic phosphate. All three phosphorylated polymers (ABA-PEG10k-Pi10, ABA-PEG16k-Pi14, and ABA-PEG20k-Pi20, 2 mM) (FIG. 3A) suppressed PstS expression indicating that Pi was available for bacteria. In contrast, the non-phosphorylated parent polymers ABA-PEG10k-GO1 (G10 means that the designed number of repeating glycerol units is 10), ABA-PEG16k-G14, and ABA-PEG20k-G20 did not suppress PstS expression demonstrating that there was no effect of the nascent ABA structure on the PstS expression via some type of non-specific interaction (FIG. 3A). Reiterative experiments were then performed that used the ΔPvdD/pstS-EGFP strain, a pyoverdin-deficient mutant derivative of MPAO1-P1 harboring pSensor-PstS-EGFP. By using this mutant, the decrease in fluorescence observed with ABA-PEG-Pis was verified as attributable to decreased PstS expression and not to the production of pyoverdin, a fluorescent compound that is also produced in this medium [23]. The pattern of PstS expression in ΔPvdD/pstS-EGFP was similar to that observed with the MPAO1-P1/pstS-EGFP (FIG. 3B). These data demonstrate that phosphorylated polymers suppress the main signal indicating phosphate limitation, i.e., PstS expression. Phosphorylated polymers did not inhibit bacterial growth (FIG. 9).

ABA-PEG-Pis Significantly Decrease Pyocyanin Production by *P. aeruginosa* Under Phosphate Limited Conditions and During Exposure to Opioids.

Figure 4:
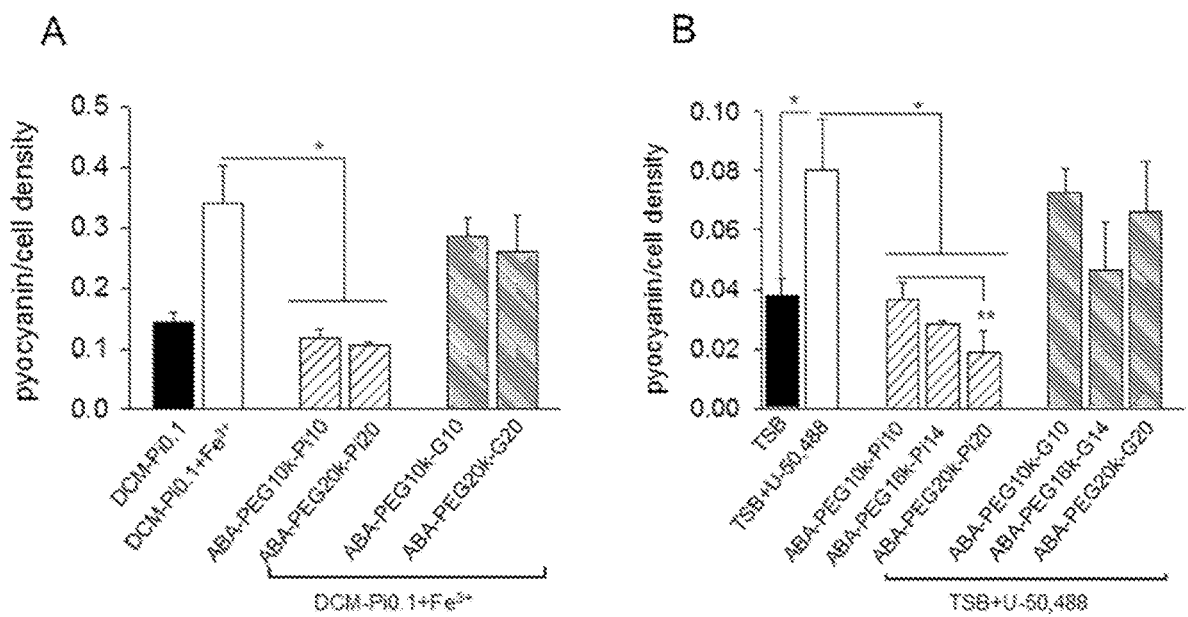
FIG. 4. ABA-Pi-PEGs significantly decrease pyocyanin production in *P. aeruginosa*. (A) Production of pyocyanin in *P. aeruginosa* MAPO1-P2 grown in phosphate/iron-limited medium DCM-Pi0.1, phosphate-limited medium DCM-Pi0.1+$Fe^{3+}$, 2 μM, and phosphate-limited/iron-enriched media supplemented with 1 mM phosphorylated and non-phosphorylated polymers. (B) Production of pyocyanin in MPAO1-P1 in TSB supplemented with 0.2 mM U-50,488 in the presence or absence of phosphorylated and non-phosphorylated polymers. n=3 per group, *p<0.01. Columns represent average values, and error bars-standard deviations.
Figure 5:
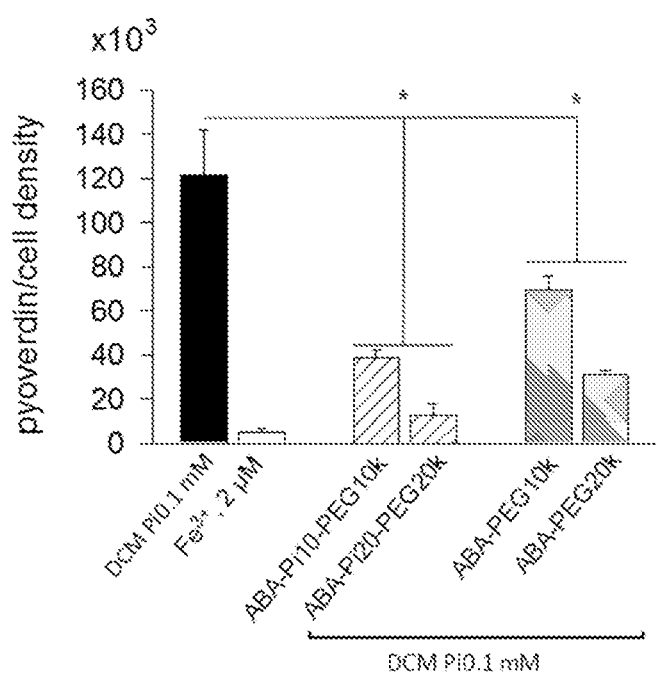
FIG. 5. ABA-Pi-PEGs and ABA-PEGs significantly decrease pyoverdin production in *P. aeruginosa*. n=3 per group, *p<0.01. Columns represent average values, and error bars—standard deviations.

One of the most distinguishing features of strains of *P. aeruginosa* is their production of pyocyanin, a water-soluble blue-green phenazine compound. Pyocyanin is one of the major toxins of *P. aeruginosa* that induces rapid apoptosis of human neutrophils, and thus defines the virulence of this highly lethal opportunistic pathogen. The production of pyocyanin is controlled by the quorum sensing system (QS), a central virulence circuit in *P. aeruginosa* and other pathogens. The PstS-PhoB phosphate regulon, a two component membrane regulator, is activated during phosphate limitation and is involved in the transcriptional activation of QS. Thus, enrichment of media with phosphate leads to suppression of pyocyanin production [23, 24]. Therefore, ABA-PEG-Pi was examined to determine whether Pi can suppress pyocyanin production in *P. aeruginosa* in phosphate-limited medium using DCM-Pi0.1. In this set of experiments, a MPAO1-P2 strain was used that produces a higher amount of pyocyanin compared to the MPAO1-P1 strain [16]. In experiments, it was found that supplementation of media with iron increased pyocyanin production in this nutrient-limited DCM media. Therefore, DCM media was supplemented with 2 µM $Fe^{3+}$ (1 µM $Fe_2(SO_4)_3$). Results demonstrated that both ABA-PEG10k-Pi10 and ABA-PEG20k-Pi20 significantly decreased pyocyanin production in *P. aeruginosa* MPAO1-P2 (FIG. 4A). The effect of non-phosphorylated compounds was significantly lower.

It has been demonstrated that endogenous opioid compounds are released into the intestine during physiologic stress and induce pyocyanin production via the quorum sensing (QS) system of virulence activation [17, 25]. The MPAO1-P1 strain was shown to be highly responsive to the synthetic kappa opioid U-50,488 in terms of pyocyanin production [17]. Consistent with previous results, pyocyanin production was demonstrated to be significantly increased in MPAO1-P1 when exposed to 200 µM of the kappa-opioid receptor agonist U-50,488 (FIG. 4B). All three ABA-PEG-Pi polymers reduced pyocyanin at the expected background level, with ABA-PEG20k-Pi20 being the most effective. The paired molecular weight non-phosphorylated polymers were less effective in these experiments, again indicating that that the phosphate content of a polymer is relevant to its suppressive effect on pyocyanin production.

Example 5

ABA-PEG-Pis Attenuated Animal Mortality Caused by *P. aeruginosa* Exposed to Opioids.

Figure 6:
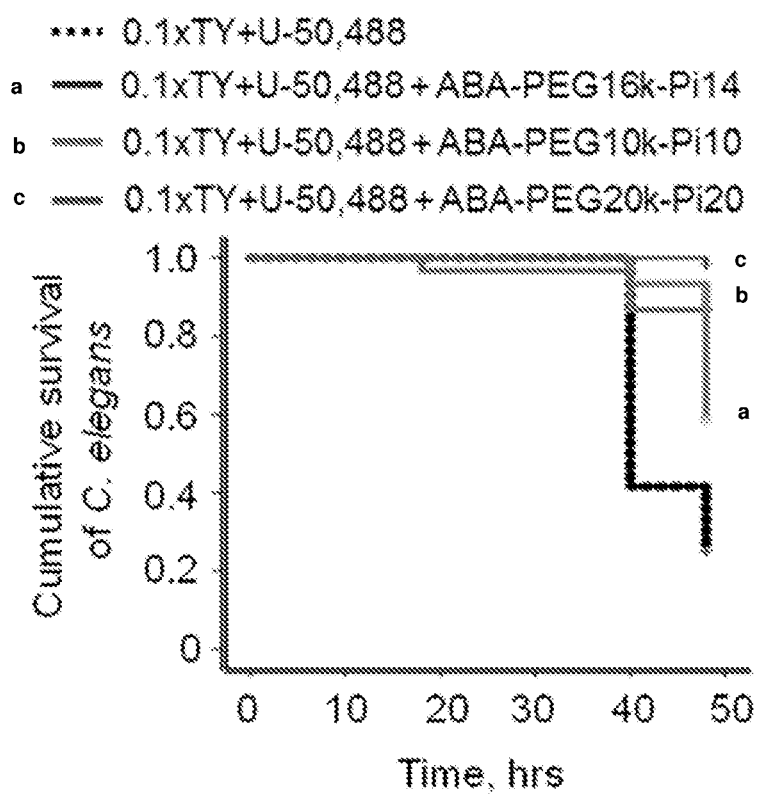
FIG. 6. Effect of each of the three phosphorylated ABA polymers on *C. elegans* survival. Experiments are performed on *C. elegans* nematodes feeding on *P. aeruginosa* in low nutrient media (0.1×TY) and exposed to opioids (U50,488) as a provocative agent known to enhance *P. aeruginosa* virulence. Kaplan-Meyer survival curves demonstrate a statistically significant (p<0.05) protective effect of all three polymers at 2 mM concentration when compared to the no treatment group. Results indicate that the ABA-PEG20k-Pi20 confers a superior protective effect compared to the remaining polymers (n=10 worms/plate (treatment group), 3 independent runs per group.
Figure 14:
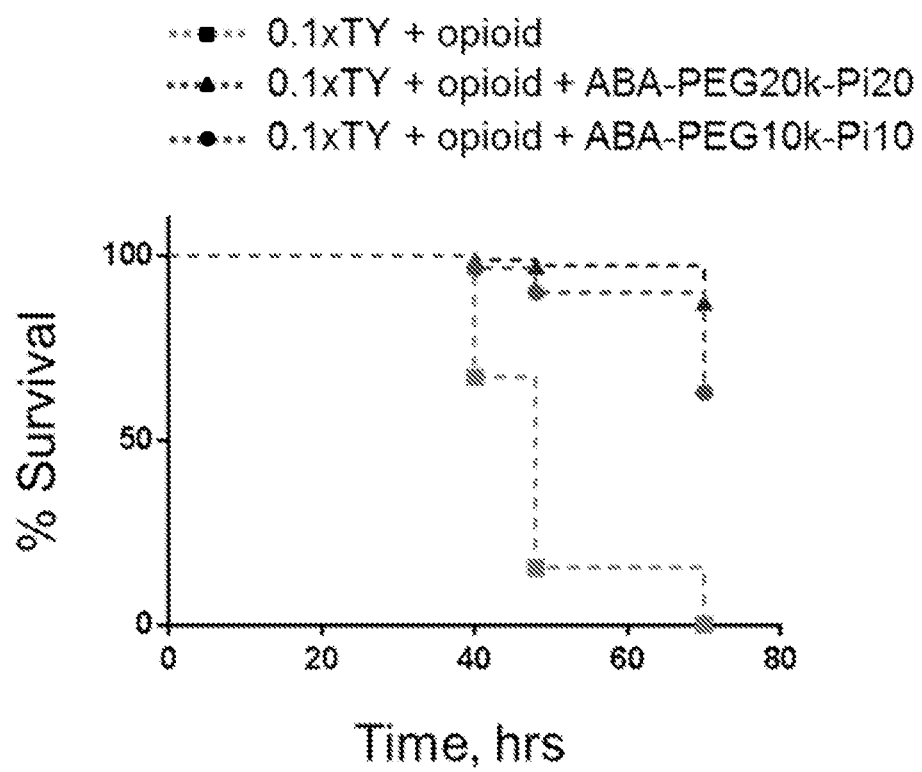
FIG. 14. Effect of phosphorylated ABA polymers on *C. elegans* survival. Experiments were performed on *C. elegans* nematodes feeding on *P. aeruginosa* in low nutrient media (0.1×TY) and exposed to opioids (U50,488) as a provocative agent known to enhance *P. aeruginosa* virulence. Kaplan-Meyer survival curves demonstrate a statistically significant (p=0.01, Log-rank Mantel-Cox test) protective effect of ABA-PEG20k-Pi20 compared to ABA-PEG10k-Pi10 at 5% concentration. Both polymers have significant protective effect compared to the no-PEG group (p<0.0001, Log-rank Mantel-Cox test). Results indicate that the ABA-PEG20k-Pi20 confers a superior protective effect compared to the remaining polymers examined in the study (n=10 worms/plate (treatment group), 3 independent runs per group).

Two animal models (i.e., small animal model of *Caenorhabditis elegans* and mouse model) were developed to assess local phosphate depletion at sites of colonization of *P. aeruginosa*, and their use validated the fidelity between these models [23, 26]. The *C. elegans* model was used in the experiments disclosed herein in which the opioid-induced lethality of *P. aeruginosa* was shown to be suppressed by the delivery of inorganic phosphate[18]. In order to test the in vivo efficacy of the de novo synthesis of APA-PEG-Pi compounds, conditions of both opioid exposure and phosphate limitation were created. Results indicated that all three ABA-PEG-Pi polymers, at equal concentrations of 2 mM, effectively decreased *C. elegans* mortality (FIG. 6) with the ABA-PEG20k-Pi20 displaying the greatest degree of protection. Because ABA-PEG20k-Pi20 carries the highest phosphate at equal molarity, to verify that the protective effect is not dependent on phosphate concentration, reiterative experiments were performed comparing ABA-PEG10k-Pi10 to ABA-PEG20k-Pi20 at concentrations of 5 weight percent. At the same weight concentration, ABA-PEG20k-Pi20 and ABA-PEG10k-Pi10 contained nearly equal quantities of phosphate. Results demonstrated that ABA-PEG20k-Pi20 still exhibited a significantly higher protective effect compared to ABA-PEG10k-Pi10 (FIG. 14), indicating that the higher molecular weight leads to a greater protective effect attributable to ABA-PEG20k-Pi20 relative to ABA-PEG10k-Pi10.

Figure 10:
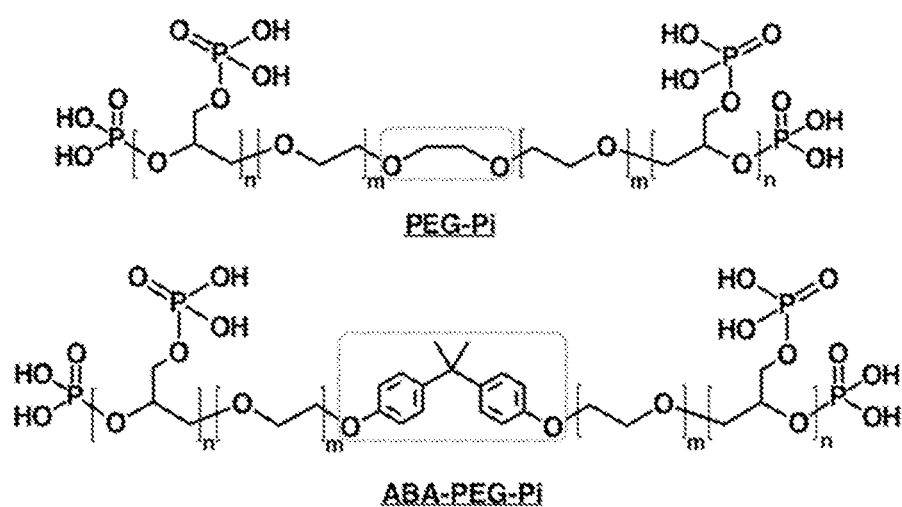
FIG. 10. Comparison of the chemical structure of phosphate-containing PEG-based block copolymers: ABA-PEG-Pi with the hydrophobic core BPA and PEG-Pi without BPA.
Figure 11:
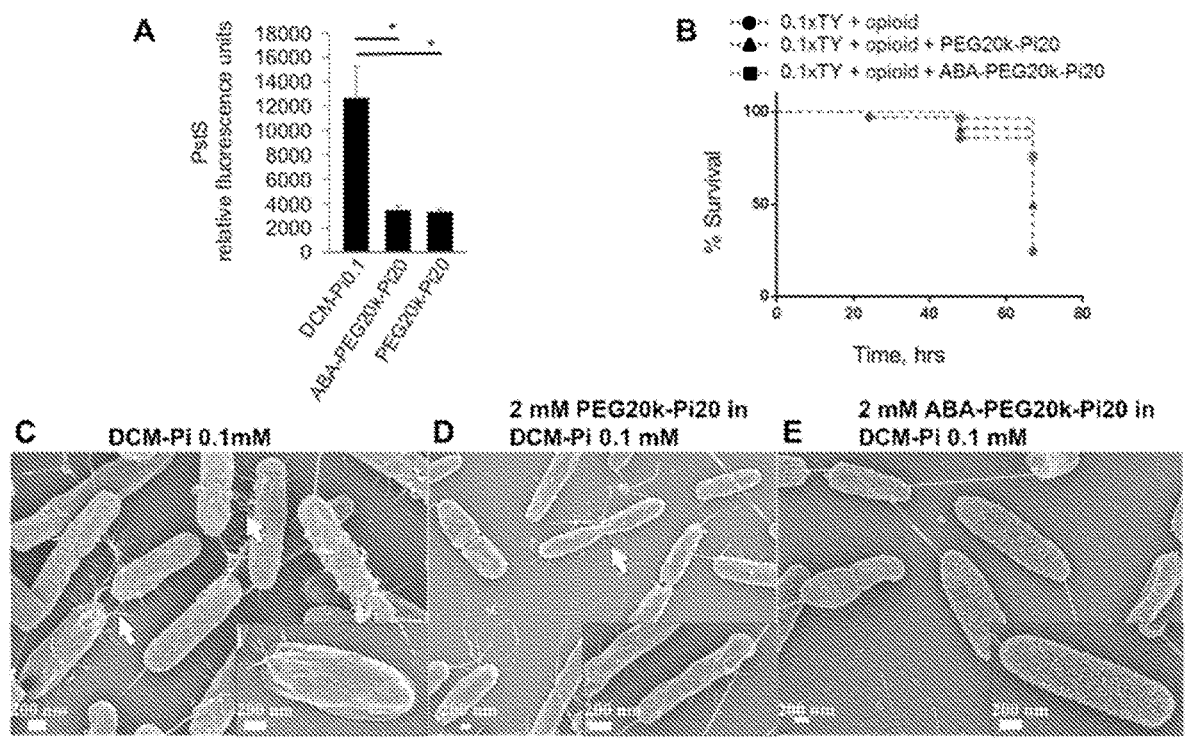
FIG. 11. The hydrophobic core BPA in ABA-PEG20k-Pi20 significantly contributes to bacterial coating and its in vivo protection against lethality. (A) PstS expression. N=3/group, *p<0.001. (B) *C. elegans* survival. N=60/group, p<0.0001 between groups (Long-rank (Mantiel-Cox) test). (C-E) Scanning electron microscopy images of *P. aeruginosa* cultured in different media. The bacteria were first cultured in different media for several hours, then immediately after washing with buffer solution, dried in a critical point dryer, coated with Pt/Pd and images taken. Arrows indicate pili-like filaments. (C), cultured in phosphate-limited (DCM Pi-0.1 mM) media only, (D) cultured in DCM Pi-0.1 mM containing 2 mM PEG20k-Pi20, and (E) cultured in DCM Pi-0.1 mM containing 2 mM ABA-PEG20k-Pi20.
Figure 12:
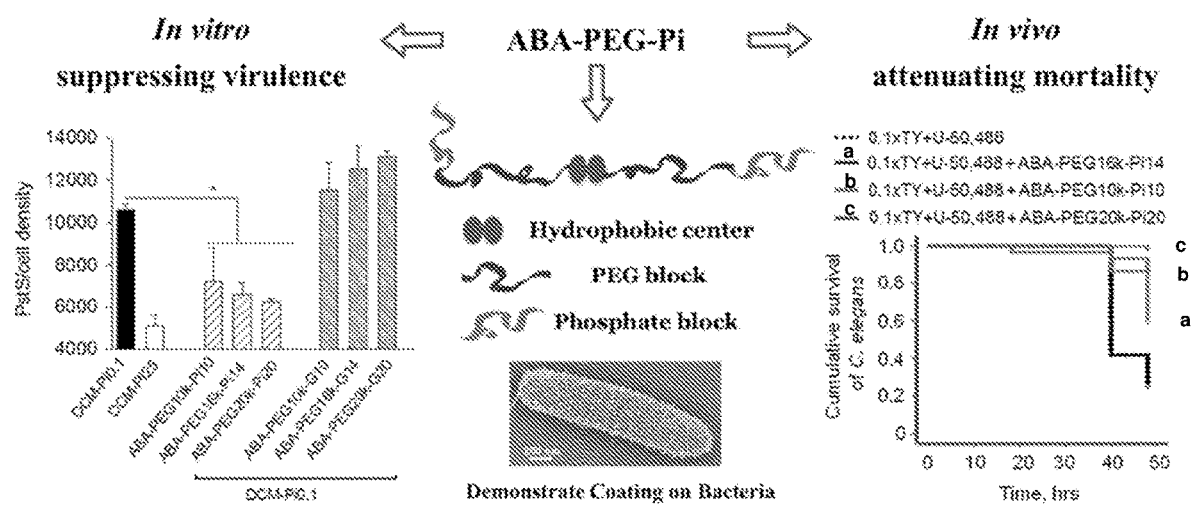
FIG. 12. Schematic illustration of ABA-PEG-Pi block co-polymer and its function suppressing virulence of pathogenic microbes in vitro and attenuation of mortality in vivo, as well as its capacity to coat the surface of bacteria. The central schematic shows a central hydrophobic core flanked by PEG blocks on each side, with terminal phosphate blocks.

The hydrophobic core BPA in ABA-PEG20k-Pi20 significantly contributed to bacterial coating and its in vivo protection against lethality. In order to confirm that it is the unique ABA structure of ABA-PEG20k-Pi20 that plays a significant role in its protective capacity, PEG20k-Pi20 was synthesized. This polymer has a similar structure to ABA-PEG20k-Pi20, but lacks the hydrophobic core (FIG. 10). As presented in FIG. 11A, results showed that both phosphorylated polymers suppressed PstS expression to the same degree, demonstrating that both can serve as phosphate delivery molecules. In *C. elegans* experiments, however, the protective effect of amphiphilic ABA-PEG20k-Pi20 was significantly greater than the protective effect of the hydrophilic PEG20k-Pi20 molecule (FIG. 11B). Because ABA-PEG-Pis may adhere to and shield the bacterial surface, the coating capacities of ABA-PEG20k-Pi20 and PEG20k-Pi20 were examined. This was performed using scanning electron microscopy (SEM) on *P. aeruginosa*. Bacteria were cultured in different media for several hours, washed with buffer solution, dried in a critical point dryer, and coated with Pt/Pd before images were taken. FIGS. 11C, 11D, and 11E display images of *P. aeruginosa* cultured in phosphate-limited (DCM Pi-0.1 mM) media only, cultured in DCM Pi-0.1 mM containing 2 mM PEG20k-Pi20 and cultured in DCM Pi-0.1 mM containing 2 mM ABA-PEG20k-Pi20, respectively. SEM images showed pili-like filaments in FIG. 11C-D (shown by arrows), while in FIG. 11E, pili-like filaments disappeared when bacteria were coincubated in the presence of ABA-PEG20k-Pi20. These findings indicate that motility appendages, key structures involved in virulence, are influenced by the composition of the two compounds [27]. In the presence of ABA-PEG20k-Pi20, the surface of bacterial cells displayed a distinct rugged appearance. It is expected that the hydrophobic linkage BPA acts as an anchor, inserting itself into the alkyl chain region of the bacterial membrane, thus firmly attaching the ABA-PEG20k-Pi20 polymer to the bacterial cell surface. In this way, amphiphilic block copolymers like ABA-PEG20k-Pi20 are expected to be advantageous as bacterial surface coating agents and hence protective in vivo.

Example 6

Oral Administration of Phosphorylated Polymers is Effective to Prevent Sepsis and Modulate Intestinal Homeostasis.

An experiment was conducted to assess the effects of phosphorylated polymers, i.e., PPi-6 and ABA-PEG20k-Pi20, delivered orally as drinking solutions to mice subjected to 30% hepatectomy and intestinal infection with the human pathogen community. More particularly, the mice were divided into the following groups. Group 1 contained starvation-positive, antibiotic-positive mice receiving no phosphorylated PEG but exposed to the pathogen community. Data from three groups of mice were analyzed. Absolute (FIG. 16A) and relative to crypt depth (FIG. 16B) Ki67 distributions were counted on 90 crypts cumulative of 3 mice in each group. Group 2 contained starvation-positive, antibiotic-positive mice receiving 3% PPi-6 and exposed to the pathogen community. Data from three mice were analyzed, totaling 109 crypts for Ki67 counts. Group 3 contained starvation-positive, antibiotic-positive mice receiving 1% ABA-PEG20k-Pi20 and exposed to the pathogen community. Data from three mice were analyzed, totaling 168 crypts for Ki67 counts.

Figure 16:
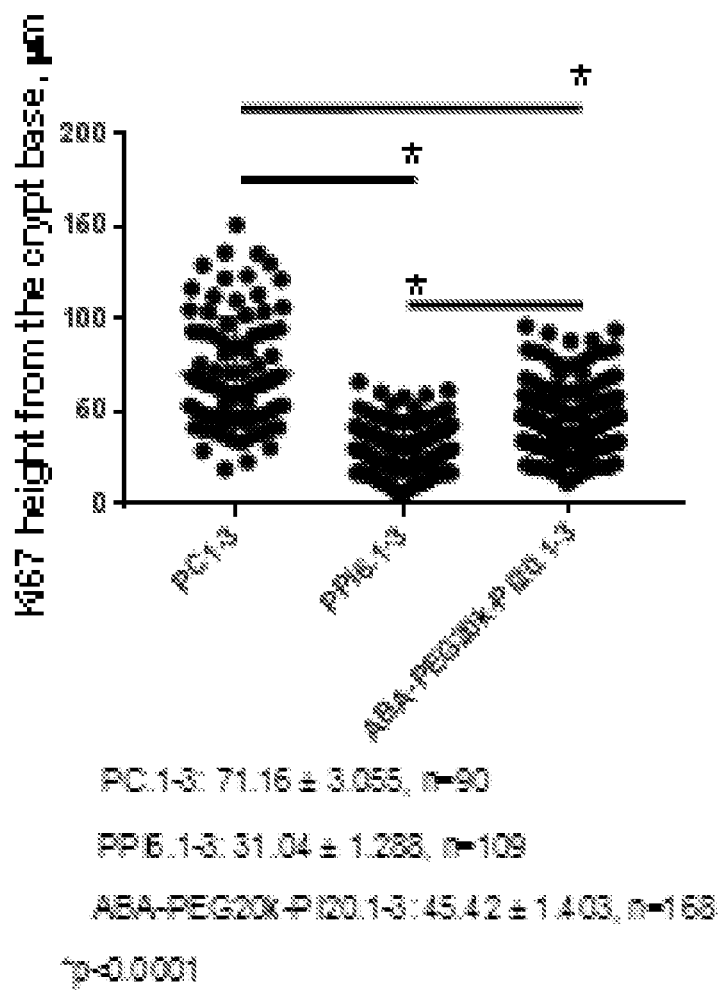
FIG. 16. Phosphorylated PEG is effective when administered orally through drinking water. (A) FIG. 10(A) provides data showing the extent of cell proliferation in cecal crypts of mice provided with drinking water lacking a phosphorylated PEG (PC 1-3, i.e., pathogen community, plates 1-3 wherein each plate contained 10 or 15 *C. elegans* worms exposed to pathogens), drinking water containing 3% PPi6 (hexametaphosphate) (PPi6 1-3 refers to plates 1-3 as described above, but exposed to pathogens from mice drinking 3% PPi6), or drinking water containing 1% ABA-PEG20k (ABA-PEG20k-P120 1-3, wherein 1-3 refers to plates 1-3 as described above exposed to pathogen from mice drinking 1% ABA-PEG20k). All groups are SAH+PC (starvation-positive, antibiotic-positive hepatectomy subjects exposed to the pathogen community), POD2 (data from post-operative day 2), and cell proliferation is measured by immunostaining for Ki67. The results reveal that cells proliferate to a height of 71.16±3.055 m above the crypt base when drinking water lacking any phosphorylated PEG. In contrast, cells proliferate to a height of 31.04±1.288 m or a height of 45.42±1.403 m above the cecal crypt base in mice drinking water containing 3% PPi6 or 1% ABA-PEG20k, respectively. (B)
Figure 16:
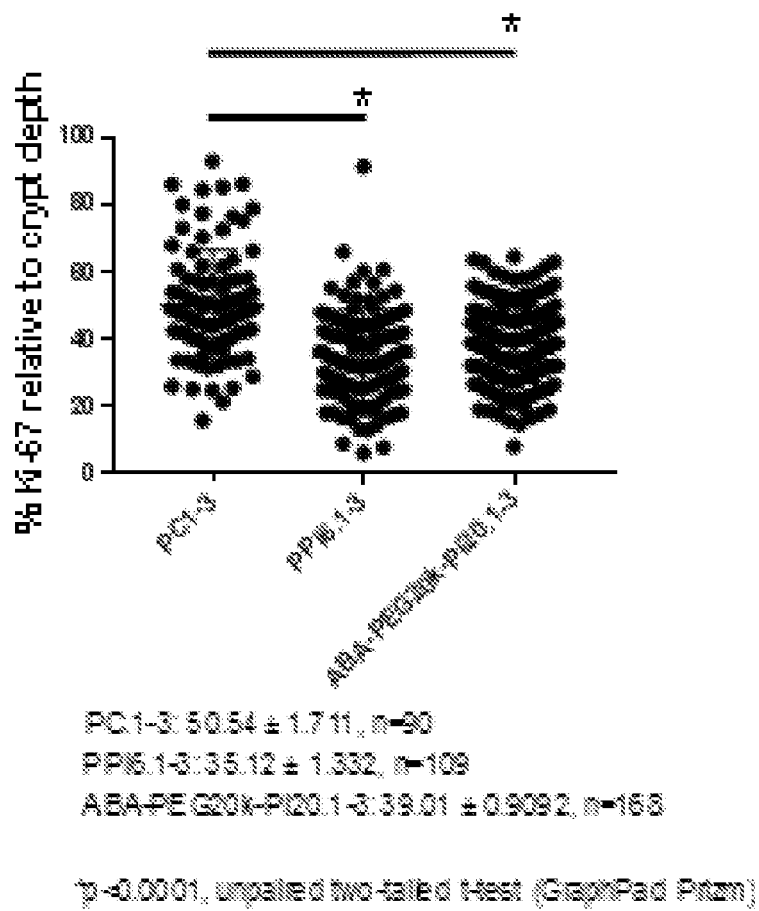

The results shown in FIGS. 16A and 16B establish that phosphorylated polymers (3% PPi6 and 1% ABA-PEG20k-Pi20) inhibit abnormal stem cell proliferation in cecal crypts of hepatectomized mice exposed to a pathogen community. Stem cell proliferation in cecal crypts, measured by immunostaining for the Ki67 marker, provides an accepted measure of crypt homeostasis. These results further demonstrated the beneficial effects of phosphorylated polymers administrations disclosed herein. In addition, mice provided with drinking water containing no phosphorylated PEG exhibited a 40% mortality rate on post-operative (hepatectomy) day 2, following exposure to the pathogen community. In contrast, mice drinking water containing 3% PPi6 or water containing 1% ABA-PEG20k-Pi20 exhibited 0% mortality rates (post-operative day 2) following exposure to the pathogen community. Thus, both phosphorylated polymers PPi-6 and phosphorylated PEGs promoted survival of mice.

Example 7

ABA-PEG-Pis Attenuated Collagenase Activity of Collagenolytic *Enterococcus faecalis* and Reduced Anastomotic Leakage Rates.

Overnight incubation of two different *Enterococcus faecalis* collagenolytic strains (E2 and E27) with 2 mM of ABA-PEG20k-Pi20 led to near complete inhibition of collagenase production in both strains (from 18,000 to 1,000 and from 68,000 to 5,000 collagenase units (n=6, p<0.001)) without suppressing bacterial growth. Next, the compound was tested in a mouse model of *E. faecalis*-mediated anastomotic leak by providing 1% ABA-PEG20k-Pi20 in drinking water. At post-operative day (POD) 7, anastomotic healing was assessed and the total amount of *E. faecalis* present at the anastomotic site and the percentage of *E. faecalis* expressing the collagenolytic phenotype were determined. Based on calculated anastomotic healing scores, leak rates were decreased from 80% to 20% in mice drinking 1% ABA-PEG20k-Pi20 (n=10, p<0.01). In ABA-PEG20k-Pi20 drinking mice, the concentration of phosphate in distal colon mucus was increased two-fold, the mean population of *E. faecalis* at the site of anastomosis was decreased 12-fold with the percentage of collagenolytic colonies in entire populations decreased from 20% (no ABA-PEG20k-Pi20) to 1% (with ABA-PEG20k-Pi20) (n=5, p<0.05).

Sodium hexametaphosphate (PPi-6) profoundly suppresses the collagenase production in gram negative strains *S. marcescens* and *P. aeruginosa* and PPi-6 supplementation in the drinking water protects mice from colonic anastomosis leakage induced by these strains. However, PPi-6 only slightly attenuated collagenase production in *E. faecalis*. As described herein, ABA-PEG20k-Pi20 suppresses collagenase activity in *E. faecalis* and promotes anastomotic healing in a mouse model of anastomotic leak caused by intestinal injection of *E. faecalis*.

Two groups of mice were involved in this study. All mice were subjected to colon anastomosis followed by an enema of *E. faecalis* E2 at POD1. The first group received water, and the second group received 1% ABA-PEG20k-Pi20 dissolved in water. At the time of sacrifice at POD7, the tissues and luminal contents were collected at the site of anastomosis, homogenized, and used for culturing. Total *Enterococcus* colonization at the anastomosis site and luminal content were determined by culture analysis using Enterococcal selective plates (BD Difco) on which all *Enterococcus* species produced black-pigmented colonies. The CFU count was normalized to the sample weight. The total *Enterococcus* population was not significantly different between the two groups in both the lumen and the tissue at the anastomotic site. The collagenolytic population was evaluated on Enterococcal plates covered with skim milk on which collagenolytic species produced black colonies with a clearing halo surrounding the colony. The amount of collagenolytic colonies of *E. faecalis* was significantly reduced by ABA-PEG20k-Pi20 in both tissue and luminal contents.

Mucus layers at anastomotic sites are enriched with phosphate in mice treated with ABA-PEG20k-Pi20. Phosphate concentration was measured in mucus layer scrapped off from 1 $cm^2$ area at the site of anastomosis at the time of sacrifice at POD7. The concentration of phosphate was significantly increased in ABA-PEG20k-Pi20 group (*E. faecalis* group 23.22±5.73 versus *E. faecalis*+ABA-PEG20k-Pi20, 48.42±7.633 µM, p=0.0297, n=5).

The non-phosphorylated parent polymer ABA-PEG20k is less effective compared to ABA-PEG20k-Pi20. The phosphorylated polymer ABA-PEG20k-Pi20 is more potent compared to its parent non-phosphorylated compound ABA-PEG20k for suppression of collagenolytic activity of *E. faecalis*. A comparative analysis was performed for ABA-PEG20k-Pi20 versus ABA-PEG20k in our mouse model and found that ABA-PEG20k is less effective compared to ABA-PEG20k-Pi20. Both anastomotic leak scores and number of collagenolytic colonies of *E. faecalis* were significantly higher in ABA-PEG20k group.

The inability of PPi-6 to suppress the collagenolytic activity of *E. faecalis* in vitro relates to its inability in vivo to improve anastomotic healing. Orally delivered 6-mer polyphosphate (PPi-6) has been recently proved as a potent protective compound in anastomotic leak induced by gram-negative collagenolytic strains of *S. marcescens* and *P. aeruginosa*. The efficacy of this compound in vivo correlated to its ability to profoundly suppress collagenase activity in these strains in vivo. However, PPi-6 does not affect the collagenolytic activity in *E. faecalis*, and does not promote a growth. Actually, PPi-6 at concentrations of >2 mM even suppressed the *E. faecalis* growth. Respectively, in in vivo experiments, the oral PPi-6 did not improve the anastomotic healing complications caused by *E. faecalis*.

Preparing a bowel is a critical step in colonic surgery. In most cases, it includes mechanical cleansing and a treatment with oral non-absorbable antibiotics. However, as it becomes evident, this procedure cannot guaranty the bacterial clearance, and there are multiple evidences that bacterial pathogens such *E. faecalis* and *P. aeruginosa* are often cultured from leaking anastomosis. These bacteria were shown to complicate anastomotic healing by degradation of collagen and thereby preventing normal extracellular matrix rearrangement that is required for wound healing. Given the emergence of multi-drug resistant bacteria, novel formulations are required for bowel preparation. Among components of a bowel preparation, those responsible for decrease of bacterial collagenolytic activities should be considered. Such components are to be directed to specific bacterial phenotype rather than to antibiotic-like effect. For this, scientific-based approaches are required. It was recently demonstrated a potency of a phosphate-based therapy using PPi-6 to improve anastomotic healing by suppressing collagenase activity of gram-negative pathogens. In the present study, it was demonstrated that a potential of yet another phosphate-based therapeutic compound, a phosphorylated triblock copolymer ABA-PEG20k-Pi20 to suppress the collagenolytic activity in gram-positive bacterium *Enterococcus faecalis*, a pathogen tightly associated with anastomotic leak. The polymer ABA-PEG20k-Pi20 was synthesized de novo and verified for its ability to coat bacteria and make its phosphate available for delivery and virulence suppression. In the present study, ABA-PEG20k-Pi20 delivers phosphate to the site of anastomosis, significantly attenuates collagenolytic populations of *E. faecalis* at anastomotic sites and enhances anastomotic healing. The ability of ABA-PEG20k-Pi20 to suppress collagenolytic activity is critical for its in vivo protective effect as its non-phosphorylated parent compound ABA-PEG20k and inorganic polyphosphate PPi-6 that were less effective for prevention of collagenolytic activity of *E. faecalis* were also less protective to prevent anastomotic leak caused by this pathogen. In some embodiments, ABA-PEG20k-Pi20 could be combined with PPi-6 to formulate a bowel preparation against broad range collagenolytic pathogens.

The disclosure provided herein, including the experimental data presented in Examples 1-7, establish that de novo synthesis of phosphorylated PEGs, e.g., ABA-PEG-Pi polymers yield compounds that exhibit anti-microbial function against *P. aeruginosa* both in vitro and in vivo, with the added benefit of allowing bacterial growth to proceed normally. It is expected that these compounds will prove efficacious against microbial pathogens of the vertebrate intestine, e.g., the mammalian, such as human, intestine, including *P. aeruginosa* and other organisms identified as causative agents of significant diseases, such as GI infections and inflammations as well as sepsis.

REFERENCES

[1] Teillant, A.; Gandra, S.; Barter, D.; Morgan, D. J.; Laxminarayan, R., Potential Burden of Antibiotic Resistance on Surgery and Cancer Chemotherapy Antibiotic Prophylaxis in the USA: a Literature Review and Modelling Study. *Lancet Infect. Dis.* 2015, 15, 1429-1437.

[2] Price, R. J.; Cuthbertson, B. H.; Su, D. c., Selective Decontamination of the Digestive Tract and Oropharynx: After 30 Years Of Debate is the Definitive Answer in Sight? *Curr. Opin. Crit. Care.* 2016, 22, 161-166.

[3] Zaborin, A.; Defazio, J. R.; Kade, M.; Kaiser, B. L. D.; Belogortseva, N.; Camp, D. G.; Smith, R. D.; Adkins, J. N.; Kim, S. M.; Alverdy, A.; Goldfeld, D.; Firestone, M. A.; Collier, J. H.; Jabri, B.; Tirrell, M.; Zaborina, O.; Alverdy, J. C., Phosphate-Containing Polyethylene Glycol Polymers Prevent Lethal Sepsis by Multidrug-Resistant Pathogens. *Antimicrob. Agents Chemother.* 2014, 58, 966-977.

[4] Vale, P. F. M., L.; Doeschl-Wilson, A.; King, K. C.; Popat, R.; Domingo-Sananes, M. R.; Allen, J. E.; Soares, M. P.; Kiimmerli, R., Beyond Killing: Can We Find New Ways to Manage Infection? *Evol. Med. Public Health* 2016, 1, 148-157.

[5] Banerjee, I.; Pangule, R. C.; Kane, R. S., Antifouling Coatings: Recent Developments in the Design of Surfaces that Prevent Fouling by Proteins, Bacteria, and Marine Organisms. *Adv. Mater.* 2011, 23, 690-718.

[6] Camps, M.; Barani, A.; Gregori, G.; Bouchez, A.; Le Berre, B.; Bressy, C.; Blache, Y.; Briand, J. F., Antifouling Coatings Influence both Abundance and Community Structure of Colonizing Biofilms: a Case Study in the Northwestern Mediterranean Sea. *Appl. Environ. Microbiol.* 2014, 80, 4821-4831.

[7] Dimitriou, M. D.; Zhou, Z. L.; Yoo, H. S.; Killops, K. L.; Finlay, J. A.; Cone, G.; Sundaram, H. S.; Lynd, N. A.; Barteau, K. P.; Campos, L. M.; Fischer, D. A.; Callow, M. E.; Callow, J. A.; Ober, C. K.; Hawker, C. J.; Kramer, E. J., A General Approach to Controlling the Surface Composition of Poly(ethylene oxide)-Based Block Copolymers for Antifouling Coatings. *Langmuir* 2011, 27, 13762-13772.

[8] Gao, Q.; Yu, M.; Su, Y.; Xie, M.; Zhao, X.; Li, P.; Ma, P. X., Rationally Designed Dual Functional Block Copolymers for Bottlebrush-like Coatings: In vitro and In vivo Antimicrobial, Antibiofilm, and Antifouling Properties. *Acta Biomater.* 2017, 51, 112-124.

[9] Zhou, Z. L.; Calabrese, D. R.; Taylor, W.; Finlay, J. A.; Callow, M. E.; Callow, J. A.; Fischer, D.; Kramer, E. J.; Ober, C. K., Amphiphilic Triblock Copolymers with PEGylated Hydrocarbon Structures as Environmentally Friendly Marine Antifouling and Fouling-release Coatings. *Biofouling* 2014, 30, 589-604.

[10] Wang, Y. P.; Pitet, L. M.; Finlay, J. A.; Brewer, L. H.; Cone, G.; Betts, D. E.; Callow, M. E.; Callow, J. A.; Wendt, D. E.; Hillmyer, M. A.; DeSimone, J. M., Investigation of the Role of Hydrophilic Chain Length in Amphiphilic Perfluoropolyether/Poly(ethylene glycol) Networks: Towards High-performance Antifouling Coatings. *Biofouling* 2011, 27, 1139-1150.

[11] Wu, L. C.; Zaborina, O.; Zaborin, A.; Chang, E. B.; Musch, M.; Holbrook, C.; Shapiro, J.; Turner, J. R.; Wu, G. H.; Lee, K. Y. C.; Alverdy, J. C., High-molecular-weight Polyethylene Glycol Prevents Lethal Sepsis due to Intestinal *Pseudomonas Aeruginosa*. *Gastroenterology* 2004, 126, 488-498.

[12] Vilar, G.; Tulla-Puche, J.; Albericio, F., Polymers and Drug Delivery Systems. *Curr. Drug Deliv.* 2012, 9, 367-394.

[13] Kolate, A.; Baradia, D.; Patil, S.; Vhora, I.; Kore, G.; Misra, A., PEG—a Versatile Conjugating Ligand for Drugs and Drug Delivery Systems. *J. Control. Release* 2014, 192, 67-81.

[14] Liechty, W. B.; Kryscio, D. R.; Slaughter, B. V.; Peppas, N. A., Polymers for Drug Delivery Systems. *Annu. Rev. Chem. Biomol. Eng.* 2010, 1, 149-173.

[15] Bergwitz, C.; Juppner, H., Phosphate Sensing. *Adv. Chronic. Kidney Dis.* 2011, 18, 132-144.

[16] Luong, P. M.; Shogan, B. D.; Zaborin, A.; Belogortseva, N.; Shrout, J. D.; Zaborina, O.; Alverdy, J. C., Emergence of the P2 Phenotype in *Pseudomonas aeruginosa* PAO1 Strains Involves Various Mutations in mexT or mexF. *J. Bacteriol.* 2014, 196, 504-513.

[17] Zaborina, O.; Lepine, F.; Xiao, G. P.; Valuckaite, V.; Chen, Y. M.; Li, T.; Ciancio, M.; Zaborin, A.; Petrof, E. O.; Turner, J. R.; Rahme, L. G.; Chang, E.; Alverdy, J. C., Dynorphin Activates Quorum Sensing Quinolone Signaling in *Pseudomonas Aeruginosa Plos Pathog.* 2007, 3, e35.

[18] Zaborin, A.; Gerdes, S.; Holbrook, C.; Liu, D. C.; Zaborina, O. Y.; Alverdy, J. C., *Pseudomonas Aeruginosa* Overrides the Virulence Inducing Effect of Opioids When it Senses an Abundance of Phosphate. *Plos One* 2012, 7, e34883.

[19] Zaborin, A.; Smith, D.; Garfield, K.; Quensen, J.; Shakhsheer, B.; Kade, M.; Tirrell, M.; Tiedje, J.; Gilbert, J. A.; Zaborina, O.; Alverdy, J. C., Membership and Behavior of Ultra-Low-Diversity Pathogen Communities Present in the Gut of Humans during Prolonged Critical Illness. *mBio* 2014, 5, e01361-01314.

[20] Li, Z. Y.; Li, P. P.; Huang, J. L., Synthesis of Amphiphilic Copolymer Brushes: Poly(Ethylene Oxide)-graft-Polystyrene. *J. Polym. Sci. A Polym. Chem.* 2006, 44, 4361-4371.

[21] Mangold, C.; Wurm, F.; Obermeier, B.; Frey, H., Hetero-Multifunctional Poly(ethylene glycol) Copolymers with Multiple Hydroxyl Groups and a Single Terminal Functionality. *Macromol. Rapid Comm.* 2010, 31, 258-264.

[22] Zhou, P.; Li, Z. Y.; Chau, Y., Synthesis, Characterization, and In Vivo Evaluation of Poly(Ethylene Oxide-co-Glycidol)-Platinate Conjugate. *Eur. J. Pharm. Sci.* 2010, 41, 464-472.

[23] Zaborin, A.; Romanowski, K.; Gerdes, S.; Holbrook, C.; Lepine, F.; Long, J.; Poroyko, V.; Diggle, S. P.; Wilke, A.; Righetti, K.; Morozova, I.; Babrowski, T.; Liu, D. C.; Zaborina, O.; Alverdy, J. C., Red Death in *Caenorhabditis Elegans* Caused by *Pseudomonas Aeruginosa* PAO1. *Proc. Natl. Acad. Sci. USA* 2009, 106, 6327-6332.

[24] Jensen, V.; Lons, D.; Zaoui, C.; Bredenbruch, F.; Meissner, A.; Dieterich, G.; Munch, R.; Haussler, S., Rhlr Expression in *Pseudomonas Aeruginosa* is Modulated by the *Pseudomonas* Quinolone Signal via PhoB-Dependent and -Independent Pathways. *J. Bacteriol.* 2006, 188, 8601-8606.

[25] Xiao, G. P.; Deziel, E.; He, J. X.; Lepine, F.; Lesic, B.; Castonguay, M. H.; Milot, S.; Tampakaki, A. P.; Stachel, S. E.; Rahme, L. G., MvfR, a Key *Pseudomonas Aeruginosa* Pathogenicity LTTR-class Regulatory Protein, Has Dual Ligands. *Mol. Microbiol.* 2006, 62, 1689-1699.

[26] Zaborina, O.; Zaborin, A.; Romanowski, K.; Babrowski, T.; Alverdy, J., Host Stress and Virulence Expression in Intestinal Pathogens: Development of Therapeutic Strategies Using Mice and *C. elegans*. *Curr. Pharm. Design* 2011, 17, 1254-1260.

[27] Merz, A. J.; So, M.; Sheetz, M. P., Pilus Retraction Powers Bacterial Twitching Motility. *Nature* 2000, 407, 98-102.

[28] A. Zaborin, J. R. Defazio, M. Kade, B. L. Kaiser, N. Belogortseva, D. G. Camp, 2nd, R. D. Smith, J. N.

Adkins, S. M. Kim, A. Alverdy, D. Goldfeld, M. A. Firestone, J. H. Collier, B. Jabri, M. Tirrell, O. Zaborina and J. C. Alverdy, Antimicrob Agents Chemother, 2014, 58, 966-977.

[29] C. Bergwitz and H. Juppner, Adv Chronic Kidney Dis, 2011, 18, 132-144.

From the disclosure herein it will be appreciated that, although specific embodiments of the disclosure have been described herein for purposes of illustration, various modifications may be made without deviating from the spirit and scope of the disclosure.

What is claimed is:

1. A triblock copolymer comprising:
   (a) a hydrophobic core; and
   (b) at least two polyethylene glycol chains,
   wherein
   at least one polyethylene glycol chain is a phosphorylated polyethylene glycol comprising more than two phosphate groups, and
   the dispersity (D) of the copolymer is less than or equal to 1.10.

2. The triblock copolymer of claim 1 wherein at least two polyethylene glycol chains are phosphorylated polyethylene glycol chains comprising an average number of more than four phosphate groups.

3. The triblock copolymer of claim 1 wherein the hydrophobic core is a carbocyclic or heterocyclic ring.

4. The triblock copolymer of claim 3 wherein the ring is aromatic.

5. The triblock copolymer of claim 3 comprising a plurality of rings.

6. The triblock copolymer of claim 3 wherein the hydrophobic core is a diphenylmethyl moiety.

7. The triblock copolymer of claim 3 wherein the hydrophobic core is a 4,4'-(propane-2,2-diyl)diphenolate salt.

8. The triblock copolymer of claim 1 wherein the copolymer has a molecular weight of at least 8,000 daltons.

9. The triblock copolymer of claim 8 wherein the copolymer has a molecular weight of at least 12,000 daltons, 15,000 daltons, 16,000 daltons, 20,000 daltons, or is between 15,000-20,000 daltons.

10. The triblock copolymer of claim 1 wherein the copolymer is in solution.

11. The triblock copolymer of claim 1 wherein the copolymer is a phosphorylated form of ABA-polyethylene glycol-polyglycidol (ABA-PEG-PGly) or ABA-polyethylene glycol-polyethoxyethyl glycidyl ether (ABA-PEG-PEEGE).

12. A method of treating anastomotic leakage comprising administering a therapeutically effective amount of a composition comprising the triblock copolymer of claim 1 to a subject in need.

13. The method of claim 12 wherein the triblock copolymer has a molecular weight of at least 8,000 daltons, 12,000 daltons, 15,000 daltons, 16,000 daltons, 20,000 daltons, or between 15,000-20,000 daltons.

14. A method of treating a gastrointestinal microbe capable of developing a virulent phenotype comprising administering an effective amount of a composition comprising the triblock copolymer of claim 1 to a subject comprising the gastrointestinal microbe.

15. The method of claim 14 wherein the triblock copolymer has a molecular weight of at least 8,000 daltons, 12,000 daltons, 15,000 daltons, 16,000 daltons, 20,000 daltons, or between 15,000-20,000 daltons.

16. The method of claim 14 wherein the gastrointestinal microbe capable of developing a virulent phenotype is *Pseudomonas aeruginosa* or *Enterococcus faecalis*.

17. A triblock copolymer comprising:
   (a) a hydrophobic core; and
   (b) at least two polyethylene glycol chains,
   wherein
   at least one polyethylene glycol chain is a phosphorylated polyethylene glycol comprising an average number of more than two phosphate groups, and
   the dispersity (D) of the copolymer is less than or equal to 1.10.

18. The triblock copolymer of claim 17 wherein the hydrophobic core is a carbocyclic or heterocyclic ring.

19. The triblock copolymer of claim 18 wherein the hydrophobic core is a diphenylmethyl moiety.

20. The triblock copolymer of claim 17 wherein the copolymer has a molecular weight of at least 8,000 daltons.

21. The triblock copolymer of claim 17 wherein the copolymer is a phosphorylated form of ABA-polyethylene glycol-polyglycidol (ABA-PEG-PGly) or ABA-polyethylene glycol-polyethoxyethyl glycidyl ether (ABA-PEG-PEEGE).

22. A method of treating anastomotic leakage comprising administering a therapeutically effective amount of a composition comprising the triblock copolymer of claim 17 to a subject in need.

23. A method of treating a gastrointestinal microbe capable of developing a virulent phenotype comprising administering an effective amount of a composition comprising the triblock copolymer of claim 17 to a subject comprising the gastrointestinal microbe.

24. The triblock copolymer of claim 1 wherein at least one polyethylene glycol chain is a phosphorylated polyethylene glycol comprising an average number of 9.8 or more phosphate groups.

* * * * *

UNITED STATES PATENT AND TRADEMARK OFFICE
CERTIFICATE OF CORRECTION

| | | |
|---|---|---|
| PATENT NO. | : 11,571,443 B2 | Page 1 of 1 |
| APPLICATION NO. | : 16/338330 | |
| DATED | : February 7, 2023 | |
| INVENTOR(S) | : Alverdy et al. | |

It is certified that error appears in the above-identified patent and that said Letters Patent is hereby corrected as shown below:

On the Title Page

In item (73) Assignee: after "The University of Chicago, Chicago, IL (US)" please insert -- UChicago Argonne, LLC, Chicago, IL, (US) --

Signed and Sealed this
Twenty-third Day of May, 2023

Katherine Kelly Vidal
*Director of the United States Patent and Trademark Office*